US009358089B2

(12) United States Patent
Earthman et al.

(10) Patent No.: US 9,358,089 B2
(45) Date of Patent: Jun. 7, 2016

(54) SYSTEM AND METHOD FOR DETERMINING STRUCTURAL CHARACTERISTICS OF AN OBJECT

(75) Inventors: James C. Earthman, Irvine, CA (US); Cherilyn G. Sheets, Newport Beach, CA (US)

(73) Assignee: Perimetrics, LLC, Newport Beach, CA (US)

( * ) Notice: Subject to any disclaimer, the term of this patent is extended or adjusted under 35 U.S.C. 154(b) by 850 days.

(21) Appl. No.: 13/163,671

(22) Filed: Jun. 18, 2011

(65) Prior Publication Data
US 2011/0311944 A1 Dec. 22, 2011

Related U.S. Application Data

(60) Provisional application No. 61/356,599, filed on Jun. 19, 2010, provisional application No. 61/442,293, filed on Feb. 14, 2011.

(51) Int. Cl.
*A61B 5/00* (2006.01)
*A61B 19/00* (2006.01)
(Continued)

(52) U.S. Cl.
CPC . *A61C 19/04* (2013.01); *A61B 9/00* (2013.01); *G01M 7/08* (2013.01); *G01N 3/30* (2013.01); *A61B 5/0048* (2013.01); *A61B 5/1111* (2013.01); *A61B 5/4547* (2013.01); *A61B 5/682* (2013.01); *A61B 2560/0425* (2013.01)

(58) Field of Classification Search
CPC ...... A61B 5/1111; A61B 9/00; A61B 5/4547; A61B 5/682; A61B 2560/0425
USPC .................. 600/587–595, 552, 553
See application file for complete search history.

(56) References Cited

U.S. PATENT DOCUMENTS 3,176,505 A 4/1965 Hendrickson
4,157,709 A * 6/1979 Schuster et al. ............. 600/572
(Continued)

FOREIGN PATENT DOCUMENTS

GB 2136569 A 9/1984
JP 09-093067 A 4/1997
(Continued)

OTHER PUBLICATIONS

Barzin, et al., Mechanical Biocompatibility of Dental Implant Materials, Proceedings of the Fourth Pacific Rim International Conference on Materials, Japanese Institute of Metals, pp. 2492-2953 (2002) (4 sheets).
(Continued)

*Primary Examiner* — Max Hindenburg
*Assistant Examiner* — Jonathan M Foreman
(74) *Attorney, Agent, or Firm* — Quan & Associates; Nancy N. Quan; Christopher Quan

(57) ABSTRACT

The present invention relates generally to a system and method for measuring the structural characteristics of an object. The object is subjected to an energy application processes and provides an objective, quantitative measurement of structural characteristics of an object. The system may include a device, for example, a percussion instrument, capable of being reproducibly placed against the object undergoing such measurement for reproducible positioning. The structural characteristics as defined herein may include vibration damping capacities, acoustic damping capacities, structural integrity or structural stability.

20 Claims, 15 Drawing Sheets

(51) Int. Cl.
  *A61B 5/103* (2006.01)
  *A61B 5/117* (2016.01)
  *A61C 19/04* (2006.01)
  *A61B 9/00* (2006.01)
  *G01N 3/30* (2006.01)
  *G01M 7/08* (2006.01)
  *A61B 5/11* (2006.01)

(56) References Cited

U.S. PATENT DOCUMENTS

| | | | |
|---|---|---|---|
| 4,231,259 A | 11/1980 | Thiruvengadam et al. | |
| 4,314,519 A | 2/1982 | Yunoki et al. | |
| 4,341,519 A | 7/1982 | Kuhn et al. | |
| 4,470,810 A | 9/1984 | Bourdeau et al. | |
| 4,482,324 A | 11/1984 | Wohlgemuth | |
| 4,499,906 A | 2/1985 | Wohlgemuth et al. | |
| 4,519,245 A | 5/1985 | Evans | |
| 4,689,011 A | 8/1987 | Wohlgemuth | |
| 4,764,114 A | 8/1988 | Jeffcoat et al. | |
| 4,963,095 A | 10/1990 | Weissman | |
| 4,979,898 A | 12/1990 | Rand | |
| 4,995,403 A | 2/1991 | Beckman et al. | |
| 5,066,142 A | 11/1991 | DeFrank et al. | |
| 5,119,803 A | 6/1992 | Fishman | |
| 5,143,069 A | 9/1992 | Kwon et al. | |
| 5,144,753 A | 9/1992 | Murphy | |
| 5,318,442 A | 6/1994 | Jeffcoat et al. | |
| 5,318,445 A | 6/1994 | Meier et al. | |
| 5,392,779 A | 2/1995 | Meredith et al. | |
| 5,402,781 A | 4/1995 | Dimarogonas | |
| 5,454,718 A | 10/1995 | Strohmaier | |
| 5,476,009 A | 12/1995 | Dimarogonas | |
| 5,518,008 A | 5/1996 | Cucchiaro et al. | |
| 5,587,284 A | 12/1996 | Brattesani | |
| 5,614,674 A | 3/1997 | Dimarogonas | |
| 5,621,398 A | 4/1997 | Blair et al. | |
| 5,652,386 A | 7/1997 | Dimarogonas | |
| 5,755,571 A | 5/1998 | Companion | |
| 5,836,891 A | 11/1998 | Dimarogonas | |
| 5,882,194 A | 3/1999 | Davis et al. | |
| 5,882,197 A | 3/1999 | Davis et al. | |
| 5,951,292 A | 9/1999 | Lee et al. | |
| 6,024,711 A | 2/2000 | Lentle et al. | |
| 6,120,466 A * | 9/2000 | Earthman | 600/590 |
| 6,149,429 A | 11/2000 | Bukowski et al. | |
| 6,213,958 B1 | 4/2001 | Winder | |
| 6,234,975 B1 | 5/2001 | McLeod et al. | |
| 6,242,063 B1 | 6/2001 | Ferrera et al. | |
| 6,274,242 B1 | 8/2001 | Onodera et al. | |
| 6,328,695 B1 | 12/2001 | Vammen et al. | |
| 6,345,909 B1 * | 2/2002 | Yam | 374/2 |
| 6,468,215 B1 | 10/2002 | Sarvazyan et al. | |
| 6,643,552 B2 | 11/2003 | Edell et al. | |
| 6,730,377 B2 | 5/2004 | Wang | |
| 6,797,198 B1 | 9/2004 | Miyashita et al. | |
| 6,818,763 B2 | 11/2004 | Vukovich et al. | |
| 6,918,763 B2 | 7/2005 | Huang et al. | |
| 6,997,887 B2 | 2/2006 | Earthman et al. | |
| 6,998,616 B2 | 2/2006 | Favro et al. | |
| 7,001,551 B2 | 2/2006 | Meredith | |
| 7,008,385 B2 | 3/2006 | Earthman et al. | |
| 7,022,076 B1 | 4/2006 | Kantorovich et al. | |
| 7,078,075 B1 | 7/2006 | Werenicz et al. | |
| 7,147,467 B2 | 12/2006 | Shoji et al. | |
| 7,217,128 B2 | 5/2007 | Atkin et al. | |
| 7,607,972 B2 | 10/2009 | Groman | |
| 7,766,656 B1 | 8/2010 | Feine | |
| 8,241,094 B2 | 8/2012 | Groman | |
| 8,435,034 B2 | 5/2013 | Gersh et al. | |
| 8,529,313 B2 | 9/2013 | Groman | |
| 8,535,300 B2 | 9/2013 | Boitor et al. | |
| 8,540,700 B2 | 9/2013 | Di Sessa et al. | |
| 2002/0143268 A1 | 10/2002 | Meredith et al. | |
| 2002/0177790 A1 | 11/2002 | Meredith et al. | |
| 2003/0191417 A1 | 10/2003 | Welt et al. | |
| 2004/0116823 A1 | 6/2004 | Earthman et al. | |
| 2005/0003323 A1 | 1/2005 | Katsuda et al. | |
| 2005/0113691 A1 | 5/2005 | Liebschner | |
| 2013/0174639 A1 | 7/2013 | Earthman et al. | |

FOREIGN PATENT DOCUMENTS

| | | |
|---|---|---|
| WO | 9116862 A2 | 11/1991 |
| WO | 2008092125 A | 7/2008 |
| WO | 2011160102 A3 | 12/2011 |

OTHER PUBLICATIONS

Koprinarov, Ivaylo, Extended European Search Report for EP 11188989.5, European Patent Office (Mar. 19, 2012) (14 sheets).

* cited by examiner

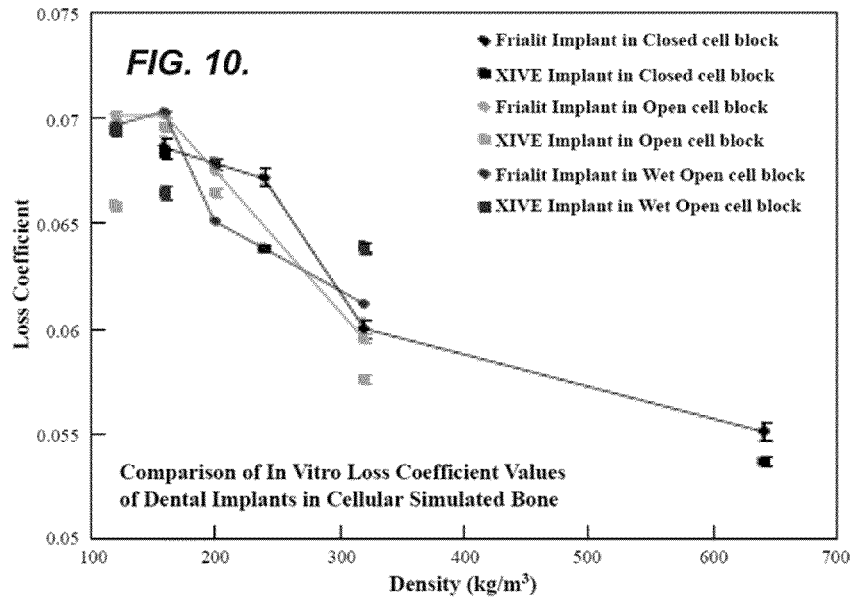
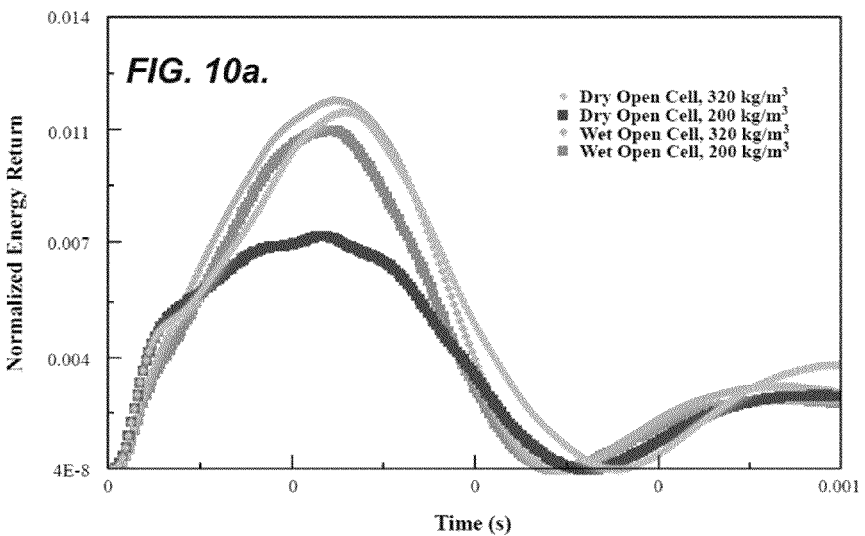
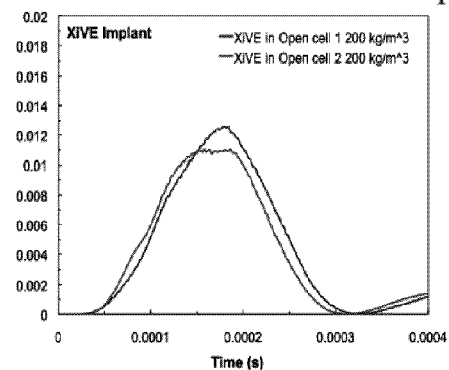
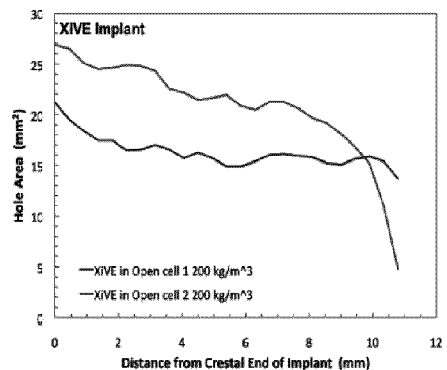
FIG. 11.                    FIG. 11a.

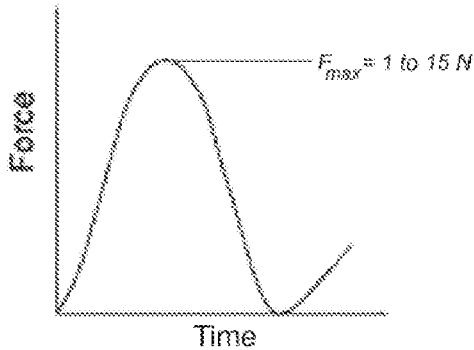
FIG. 12.
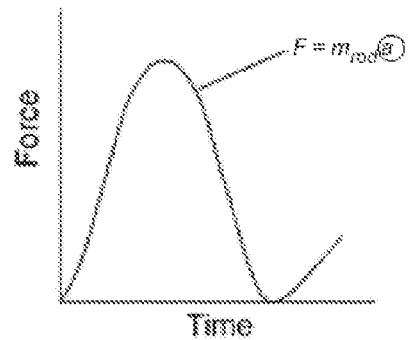
FIG. 13.
$$D = \frac{-\pi \sigma^2}{E_{loss}} = \frac{-\pi F^2}{E_{loss} A_{rod}} = \frac{-\pi (m_{rod} a)^2}{E_{loss} A_{rod}} = -C_1 a^2$$
○ $E_{loss}$, $A_{rod}$, $m_{rod}$ ≅ constants
○ $D_{int} = D - D_{ext}$
⇒ $D_{int} = C_1 a^2 - D_{ext} \cong -C_2 - C_1 a^2$
FIG. 14.
Loss Coefficient: $\eta = \dfrac{E_{loss}}{E_{elastic}} = \dfrac{D_{int}}{2\pi U} = -C'_2 - C'_1 a^2$
FIG. 15.
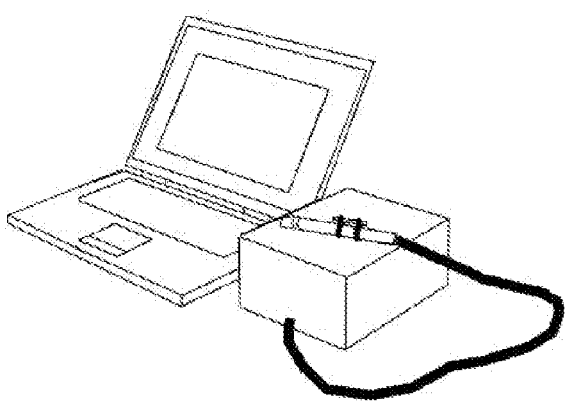
FIG. 16.
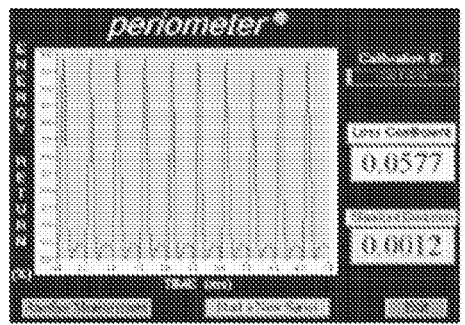
FIG. 16a.

SYSTEM AND METHOD FOR DETERMINING STRUCTURAL CHARACTERISTICS OF AN OBJECT

CROSS-REFERENCE TO RELATED APPLICATIONS

This application claims the priority and benefit of U.S. provisional patent application Ser. No. 61/356,599, filed Jun. 19, 2010, entitled "SYSTEM AND METHOD FOR DETERMINING STRUCTURAL CHARACTERISTICS OF AN OBJECT", and of U.S. provisional patent application Ser. No. 61/442,293, filed Feb. 14, 2011, entitled "SYSTEM AND METHOD FOR DETERMINING STRUCTURAL CHARACTERISTICS OF AN OBJECT", the contents of all of which are hereby incorporated by reference in their entirety.

FIELD OF THE INVENTION

This invention relates generally to evaluation of the structural properties of an object; and more specifically relates to evaluation of the structural characteristics that reflects the integrity of an object; after subjecting to an energy application thereon.

BACKGROUND OF THE INVENTION

When an object is subjected to an impact force, a stress wave is transmitted through the object. This stress wave causes deformations in the internal structure of the object. As the object deforms it acts, in part, as a shock absorber, dissipating a portion of the mechanical energy associated with the impact. The ability of the object to dissipate mechanical energy, commonly referred to as the "damping capacity" of the object, depends on several factors, including the type and structural integrity of the materials making up the object.

There are instruments that are capable of measuring the damping capacity of an object. An example of such an instrument is described in U.S. Pat. No. 6,120,466 ("the '466 patent"), issued 19 Sep. 2000 and entitled "System and Method for Quantitative Measurements of Energy Damping Capacity". The instrument disclosed in the '466 patent provides an objective, quantitative measurement of the damping capacity of an object, referred to as the loss coefficient 17. The energy of an elastic wave attenuates relatively quickly in materials with a relatively high loss coefficient, whereas the energy of an elastic wave attenuates relatively slowly in materials with a relatively low loss coefficient.

The damping capacity of an object is an important parameter in a wide variety of applications. For example, in the field of dentistry, when a healthy tooth is subjected to an impact force, the mechanical energy associated with the impact is primarily dissipated by the periodontal ligament. Changes in the structure of the periodontal ligament that reduce its ability to dissipate the mechanical energy associated with an impact force, and thus reduce overall tooth stability, can be detected by measuring the loss coefficient of the tooth.

SUMMARY OF THE INVENTION

The present invention relates to a system and method for measuring structural characteristics of an object. The object may be subjected to an energy application process and the system is adapted for providing an objective, quantitative measurement of structural characteristics of the object after the energy application process. The system and method is capable of generating more reproducible measurements and better able to detect any abnormalities that may be present in an object.

The system may include a device, for example, a percussion instrument, capable of being reproducibly placed directly on the object undergoing such measurement for reproducible measurements. The structural characteristics as defined herein may include vibration damping capacities; acoustic damping capacities; defects including inherent defects in, for example, the bone or the material that made up the object; cracks, micro-cracks, fractures, microfractures; loss of cement seal; cement failure; bond failure; microleakage; lesions; decay; structural integrity in general or structural stability in general. For an anatomical object, such as a tooth structure, a natural tooth, a natural tooth that has a fracture due to wear or trauma, a natural tooth that has become at least partially abscessed, or a natural tooth that has undergone a bone augmentation procedure, a prosthetic dental implant structure, a dental structure, an orthopedic structure or an orthopedic implant, such characteristics may indicate the health of the object, or the health of the underlying foundation to which the object may be anchored or attached. The health of the object and/or the underlying foundation may also be correlated to densities or bone densities or a level of osseointegration; any defects, inherent or otherwise; or cracks, fractures, microfractures, microcracks; loss of cement seal; cement failure; bond failure; microleakage; lesion; or decay. For objects in general, for example, polymeric composite structures including honeycombs or layered honeycombs or metallic composite structures; planes, automobiles, ships, bridges, buildings, industrial structures including, but not limited to power generation facilities, arch structures, or other similar physical structures; such measurements may also be correlated to any structural integrity, or structural stability, such as defects or cracks, even hairline fractures or microcracks, and so on.

In one exemplary embodiment, the device may include a handpiece having a housing with an open end and an energy application tool, for example, a tapping rod, or impact rod mounted inside the housing for axial movement. The housing has a longitudinal axis and the energy application tool has a length with a retracted form and an extended form, the retracted form being retracted from or substantially coextensive with the open end of the housing. The movement of the energy application tool, for example, a tapping rod, may be effected by a drive mechanism mounted inside the housing for driving the tapping rod axially within the housing between a retracted position and an extended position during operation. In the extended position, the free end of the tapping rod is capable of extending or protruding from the open end of the housing.

The drive mechanism may be an electromagnetic mechanism, and may include an electromagnetic coil. In one embodiment, the drive mechanism may include a permanent magnet secured to the back end of the energy application tool, for example, the tapping rod, and the magnetic coil may lie axially behind this permanent magnet. Together with the back part of the handpiece housing and any electrical supply lines, the magnetic coil forms a structural unit which may be integrally operational and which may be, for example, connected to the remaining device by a suitable releasable connection, for example, a screw-type connection or a plug-type connection. This releasable connection may facilitate cleaning, repairing and others.

The energy application tool, such as the tapping rod, is located in the front part of the housing and the mounting mechanism for the tapping rod may include frictionless bearings. These bearings may include one or more axial openings so that the neighboring chambers formed by the housing and the tapping rod are in communication with one another for the exchange of air.

In one embodiment, the tapping rod may have a substantially constant cross-sectional construction over its entire length, with a permanent magnetic ensemble mounted at the end away from the free end, as noted above. The electromagnetic coil of the driving mechanism may be situated behind the other end of the tapping rod, also as noted above, resulting in a relatively small outside diameter for the handpiece. In this embodiment, the outside diameter of the handpiece housing may be substantially defined only by the cross-section of the tapping rod, the mounting mechanism of the tapping rod in the housing, and the thickness of the walls of the housing.

The handpiece itself may be tethered to an external power supply or be powered by an electrical source included inside the housing, such as, for example, a battery, a capacitor, a transducer, a solar cell, an external source and/or any other appropriate source.

In one embodiment, communication between the drive mechanism and the energy application tool, such as the tapping rod, may be via a lead or line of electrically conductive, insulated wire which may be wound spirally in a concentric fashion around the tapping rod and has spring-elastic properties. This may also allow a minimum space requirement with respect to the line management. In addition, a helical spring, which may be formed by the spirally wound wire, may help to avoid or prevent looping or twisting of the wire connection.

The helical spring may be composed of stranded wires having two twisted individual wires or of a coaxial line. In its loaded condition, the spring may be compressed to such a degree that the force of its prestress corresponds to the frictional force and opposes this frictional force during the forward motion of the energy application tool, for example, the tapping rod from the retracted position to the extended position. The prestressed path of the spring may therefore be far greater than the stroke of the tapping rod so that spring power remains substantially constant over the entire stroke of the tapping rod. Any undesirable frictional force of the bearings of the mounting mechanism for the tapping rod during the forward motion may also be substantially compensated by this spring.

In one aspect, the drive mechanism may include a measuring device, for example, a piezoelectric force sensor, located within the handpiece housing for coupling with the energy application tool, such as the tapping rod. The measuring device is adapted for measuring the deceleration of the tapping rod upon impact with an object during operation, or any vibration caused by the tapping rod on the specimen. The piezoelectric force sensor may detect changes in the properties of the object and may quantify objectively its internal characteristics. Data transmitted by the piezoelectric force sensor may be processed by a system program, to be discussed further below.

In another aspect, the drive mechanism may include a linear variable differential transformer adapted for sensing and/or measuring the displacement of the energy application tool such as the tapping rod, before, during and after the application of energy. The linear variable differential transformer may be a non-contact linear displacement sensor. The sensor may utilize inductive technology and thus capable of sensing any metal target. Also, the noncontact displacement measurement may allow a computer to determine velocity and acceleration just prior to impact so that the effects of gravity may be eliminated from the results.

Located at the open end of the housing is a sleeve. The sleeve may attach and/or surround at least a length of the free end of the housing and protrudes from the housing at a distance substantially coextensive with the end of the tapping rod in its extended form. Thus, the length of the sleeve may be dependent on the length of protrusion of the extended tapping rod desired. The free end of the sleeve may be placed against an object undergoing measurement. The contact by the sleeve helps to stabilize the handpiece on the object. In one embodiment, the housing may be tapered towards the end surrounded by the sleeve so that the device may have a substantially uniform dimension when the sleeve is attached. In another embodiment, the housing may have a substantially uniform dimension and the sleeve may expand the dimension of the end it surrounds to a certain extent. In a further embodiment, the sleeve itself may have an inverse taper towards its free end to increase the flat area of contact with the object.

In one exemplary embodiment, the sleeve includes a tab protruding from a portion of its end so that when the open end of the sleeve is in contact with at least a portion of a surface of the object undergoing the measurement, the tab may be resting on a portion of the top of the object. The tab and the sleeve together assist in the repeatable positioning of the handpiece with respect to the object, thus results are more reproducible than without the tab. In addition, the tab may be adapted for repetitively placed substantially at the same location on the top of the object every time. In one embodiment, the tab may be substantially parallel to the longitudinal axis of the sleeve.

In another exemplary embodiment, the sleeve include a tab and a feature, for example, a ridge, protrusion or other feature substantially orthogonal to the surface of the tab on the side adapted for facing the surface of an object. For example, for teeth, the ridge or protrusion may nest between adjacent teeth or other orthogonal surface and may thus aid in preventing any substantial lateral or vertical movement of the tab across the surface of the object and/or further aid in repeatability. The tab may be of sufficient length or width, depending on the length or width of the top portion of the object so that the ridge or protrusion may be properly located during operation. Again, the tab and the feature also aid in the reproducible results than without the tab.

In one aspect, for example, if the object is a tooth, the feature may be short and of a sufficiently small thickness so that it may fit between adjacent teeth. In another aspect, for example, if the object is a tooth, the feature may be short and shaped to fit between the top portion of adjacent teeth. In yet another aspect, for example, if the object is a tooth, and the feature is to rest against the back or front surface, it may be of a dimension to cover a major portion of the back or front surface while the tab rests on the top surface of a tooth.

The tab and/or tab and feature not only serve to aid in repeatable positioning of the instrument on an object, such as a tooth or mechanical or industrial structure, composites and similar, as mentioned above, but the tab and/or tab and feature also serve to help keep the object, such as a tooth or mechanical or industrial structure, composites and similar, as mentioned above, from moving in directions other than the direction parallel to the energy application or tapping direction. This helps to minimize any unnecessary disturbances of the object and/or the foundation it is anchored to and/or complications which may arise from these other disturbances during testing, thus further contributing to the sensitivity and/or accuracy of detection.

The end of the sleeve not having the tab protruding from it may be flat or substantially flat and the part of the tab in contact with the top of the object may be also flat or substantially flat. The tab may extend in a substantially parallel direction from the end of the sleeve. In one aspect, the tab may be integral with the sleeve for a distance before protruding from the end of the sleeve, keeping substantially the cross-sectional outline of the sleeve after protruding from the sleeve. In another aspect, the tab may protrude uniformly from the top or bottom portion of the sleeve, but with a substantially different cross-sectional outline from that of the sleeve after protruding from the sleeve.

In one exemplary embodiment of the present invention, the tab may have a contact surface substantially mirroring the contour of the surface of an object to which it comes into contact during use for aiding in reproducibly positioning of the device directly on an object.

In one embodiment, the protruding portion of the tab may have a rectangular cross-section. In another embodiment, the protruding portion of the tab may have a slight arched top portion. In yet another embodiment, the protruding portion of the tab may conform to the contour of the surface which comes into contact with the object.

In any of the embodiments, the corners of the tab are smooth or rounded or substantially smooth or rounded to avoid any catching on the object they may be resting on.

In general, the present device may be useful in making any measurements whereby vibration is generated through the application of energy, for example, striking of, such as a tapping rod, on an object. The advantages are that the device may be held in contact with the object during the tapping action, in contrast to traditional devices that are not in contact.

The sleeve and the tab, and/or the sleeve, the tab and the feature, may be made of any material having vibration damping, acoustic damping, or vibration attenuating properties and the sleeve may be of such length so that any vibration traveling through the sleeve to the housing of the handpiece may be substantially attenuated. In one embodiment, the sleeve and the end of the housing adjacent to the sleeve may be made of the same material. In another embodiment, the sleeve and the end of the housing it is attached to may be made of materials having similar vibration attenuating properties. In yet another embodiment, the sleeve and the end of the housing it is attached to may be made of different materials. In a further embodiment, the sleeve and the end of the housing it is attached to may be made of materials having different vibration attenuating properties. In yet a further embodiment, the sleeve may be made of any material with a vibration attenuating coating on its surface or surfaces. In still yet another embodiment, the sleeve, tab and/or feature may be made of different materials having similar thermal expansion properties.

In addition, the sleeve and tab and/or the sleeve, the tab and the feature may be made of recyclable, compostable or biodegradable materials are especially useful in those embodiments that are meant to be disposed of after one use.

The evaluation of such structural characteristics mentioned above may be done in a number of methods, using a number of instruments, for example, a suitable instrument is as described in U.S. Pat. No. 6,120,466 ("the '466 patent"), issued 19 Sep. 2000 and entitled "System and Method for Quantitative Measurements of Energy Damping Capacity", incorporated herein by reference. Other instruments and methods may include such as those disclosed in U.S. Pat. Nos. 6,997,887 and 7,008,385, the contents of all of which are hereby incorporated by reference in their entirety. These measurements may include using an instrument to measure, for a time interval, energy reflected from the object as a result of the tapping or applying energy, which may include creating a time-energy profile based on the energy reflected from the object during the time interval, and/or evaluating the time energy profile to determine the damping capacity of the object. Further device may also be used, such as that disclosed U.S. Pat. Nos. 4,482,324 and 4,689,011, incorporated herein by reference in their entirety. All these instruments and devices may be modified with the present sleeve configuration for repetitive repositionability.

The sleeve in any of the above noted embodiments may be removable. According to one embodiment of the invention, the sleeve may be disposable. According to another embodiment of the invention, the sleeve may be reusable. In one aspect, the disposable sleeve may be sterilizable and disposable after multiple uses. In another aspect, the sleeve may be for a one-use, either made of sterilizable or non-sterilizable material.

The sleeve may be attached to the housing by any suitable attachment modes including, but are not limited to, threaded attachment, friction fit, mating bayonet formations, tongue and groove type formations, snap fit, internesting pin and pinhole formations, latches and other interconnecting structures. In one exemplary embodiment, the sleeve and the housing may be a custom-made threaded system for better fit.

According to another embodiment of the invention, the sleeve may be fitted to other commercially available handpieces that are not adapted for contact with an object under measurement, so that the advantages of the present invention may also be realized.

As noted above, the handpiece may be part of a system that includes computerized hardware and instrumentation software that may be programmed to activate, input and track the action and response of the handpiece for determining the structural characteristics of the object. The hardware may include a computer for controlling the handpiece and for analyzing any data collected, for example, the deceleration of the energy applying tool, for example, the tapping rod, upon impact with a object. In one embodiment, the handpiece and hardware may communicate via a wire connection. In another embodiment, the handpiece and hardware may communicate via a wireless connection.

In one embodiment, the energy application process of the handpiece may be triggered via a mechanical mechanism, such as by a switch mechanism. In one aspect, a finger switch may be located at a convenient location on the handpiece for easy activation by the operator. In another aspect, the switch mechanism may be triggered by applied pressure to the object through the sleeve. In another embodiment, the energy application process of the handpiece may be triggered via voice control or foot control.

Upon activation, the tapping rod extends at a speed toward an object and the deceleration of the tapping rod upon impact with the object may be measured by a measuring device, for example, a piezoelectric force sensor, installed in the handpiece, and transmitted to the rest of the system for analysis. In one aspect, the tapping rod may be programmed to strike an object a certain number of times per minute at substantially the same speed and the deceleration information is recorded or compiled for analysis by the system.

The sleeve and/or a portion of the housing may also have an antimicrobial coating coated thereon capable of eliminating, preventing, retarding or minimizing the growth of microbes, thus minimizing the use of high temperature autoclaving process or harsh chemicals and may increase the kind and number of materials useful as substrates for making such tools or instruments.

Further, the instrument may be useful in aiding in the selection of material, such as mechanically biocompatible material, or biomemetically compatible material used in the construction of and/or selection of a material for an anatomical structure, for example, an implant. For normal healthy teeth, the percussive energy generated by mastication is attenuated by the periodontal ligament at the healthy bone-natural tooth interface. However when an implant replaces natural tooth due to damage or disease, the ligament is generally lost and the implant may transmit the percussive forces directly into the bone. Several materials such as composites, gold, zirconia and so on, used to fabricate the implant abutment have been shown to be effective in numerous studies. While studies have demonstrated the survivability of implant restorations utilizing composite resin, gold or zirconia abutments after construction of the abutments, there has been no such research done to measure the dynamic response to load of said abutment materials. The instrument of the present invention may be used for such purposes and may be useful to predict the suitability or compatibility prior to implantation, or to choose suitable materials to protect natural teeth adjacent the implants. Thus, the choice of materials may minimize the disparity between the way the implants and natural teeth handle impact.

Furthermore, the instrument may be useful in aiding in the selection of material, such as mechanically or chemically durable or compatible material, used in the construction of and/or selection of a material for, for example, a plane, an automobile, a ship, a bridge, a building, any industrial structures including, but limited to power generation facilities, arch structures, or other similar physical structures or damping material suitable to aid in the construction of such structures. The instrument of the present invention may be used to such purposes and may be useful to predict the suitability of a material prior to construction in addition to detection of cracks, fractures, microcracks, cement failures, bond failures or defect location, etc., after the construction.

In addition, the present invention is also useful in distinguishing between defects inherent in the material making up the structure or object, and cracks or fractures, etc., as discussed above due to trauma or wear or repeated loading. Defects inherent in the bone or material construction of an implant, or a physical structure, for example, may include lesions in the bone, similar defects in the implant construction or manufacturing of polymer, polymer composites or alloys, or metallic composites or alloys.

The stabilization of the instrument by the tab or the tab and/or feature may also minimize any jerky action that may confound the testing results, for example, any defects inherent in the bone structure or physical or industrial structure may be masked by jerky action of the tester. This type of defect detection is important because the location and extent of the defect may impact dramatically upon the stability of the implant or physical or industrial structures. Generally when lesions are detected, for example, in an implant, such as a crestal or apical defect, the stability of the implant may be affected if both crestal and apical defect are present. In the past, there is no other way of gathering this type of information other than costly radiation intensive processes. With the present invention, this type of information may be gathered, and may be done in an unobtrusive manner.

In general, the present invention further represents a new form of precision of risk assessment in dental health or structural integrity of physical structures and an opportunity to diagnose in a new manner. The present invention provides for the administering of kinetic energy to the specimen, loading and displacement rates that may be determined by the specimen, deceleration measured upon impact and analysis of dynamic mechanical response for more accurate prediction of cracks, fractures, microcracks, microfractures; loss of cement seal; cement failure; bond failure; microleakage; lesions; decay; structural integrity in general; structural stability in general or defect location.

Further, multiple indicators of structural integrity, such as LC (loss coefficient) and ERG (energy return graph) may be possible as well as percussion loads in a critical direction. The present system provides a convenient and easy way of providing buccal loading and other loading directions are possible such as the lingual direction for testing the structural properties mentioned above.

Buccal loading is important in that it is typically the more dangerous type of loading encountered by, for example, a tooth. In general, vertical loading induces relatively low stresses in teeth. However, working and/or nonworking motion produces side loading as a result of the lateral motion of the jaw and inclined geometries of the occlusal surfaces of teeth and restorations. This side loading may induce much higher stress concentrations at external and internal surfaces and below the margin. Thus, using the system of the present invention, such tests may be easily performed. In short, the system not only is adapted for detection of structural stability, integrity, cracks, etc., of a prosthetic dental implant structure, a dental structure, an orthopedic structure, or an orthopedic implant, but may also be adapted for use in the actual construction and replacement process through testing under stresses that may be encountered later after implantation.

Natural loading is typically pulsatile (as opposed to for example sinusoidal). Muscular, cardiovascular, running, jumping, clenching/bruxing, so on, all may produce loading, for example, pulsatile loading. Percussion loading is pulsatile and therefore physiological. Percussion loading may be used to measure visco-elastic properties and detect damage in a structure.

As mentioned above, the present invention provides the ease and speed of application and may be employed to detect and assess microleakage, gross recurrent decay, loose post/build-up, decay in post space, whether tooth is non-restorable, gross decay, near pulp exposure, enamel and dentinal cracks, internal alloy fracture, or even any bioengineering mismatch, any defect that create movement within the structure, and so on in a non-destructive manner. This is also true of industrial or physical structures noted above.

In addition, as noted above, the present invention also contributes to the accuracy of the location of detection of defects, cracks, micro-cracks, fractures, microfracture, leakage, lesions, loss of cement seal; microleakage; decay; structural integrity in cement failure; bond failure; general or structural stability in general.

The present invention may be further exemplified by the following detailed description of the embodiments and drawings shown below.

BRIEF DESCRIPTION OF THE DRAWINGS

FIGS. 2e and 2f each illustrates a side cross-sectional view of an embodiment of a sleeve and tab of FIGS. 2a and 2f of the present invention;

FIGS. 10, 10a, 11 and 11a show graphs of an in vitro study of bone densities of four threaded titanium implants using the system and method of the present invention;

FIG. 12 shows the force being applied during impact by the tapping rod of an instrument of the present invention;

FIG. 13 shows the dynamic response of the object upon impact by the tapping rod of the instrument of the present invention;

FIGS. 14 and 15 show the formulae used in calculating loss coefficient and energy return graphs of an ideal situation;

FIG. 16 shows an instrument of the present invention;

FIG. 16a shows the loss coefficient and energy return graphs generated after impact by the tapping rod of the present invention and how it compares with the ideal fit;

DETAILED DESCRIPTION OF THE INVENTION

Figure 1:
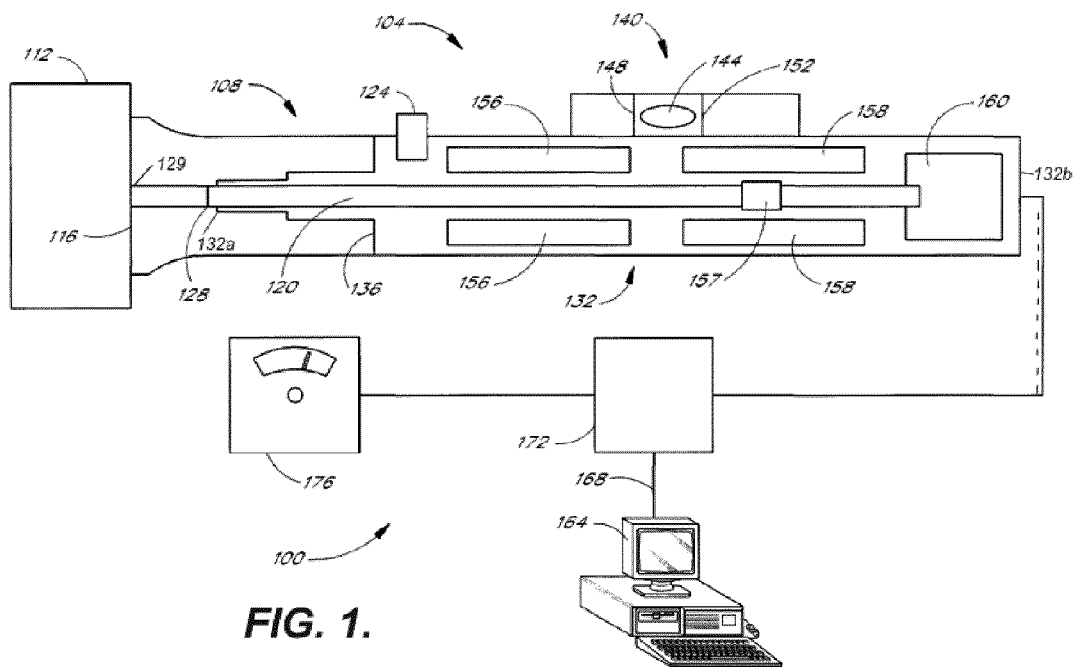
FIG. 1 illustrates a perspective view of an embodiment of a system of the present invention.

The detailed description set forth below is intended as a description of the presently exemplified systems, devices and methods provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplary methods, devices and materials are now described.

All publications mentioned herein are incorporated herein by reference for the purpose of describing and disclosing, for example, the designs and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The present invention may be used to test objects of practically any size and shape, to obtain information on their structural characteristic. Such structural characteristics not only include the physical characteristics of an object or the foundation the object may be anchored to, but also information as to their locations, compatibility or suitability of a material for use in dental work prior to the actual work, whether a tooth structure is restorable prior to the actual work, whether a restorative procedure is successful, when the tooth structure that underwent any procedure has been remodeled, the looseness of tooth structure before and after dental work, and combinations thereof.

The structural characteristics as defined herein may include vibration damping capacities; acoustic damping capacities; defects including inherent defects in, for example, the bone or the material that made up the object; cracks, micro-cracks, fractures, microfractures; loss of cement seal; cement failure; bond failure; microleakage; lesions; decay;

structural integrity in general or structural stability in general. For an anatomical object, such as a tooth, a natural tooth, a prosthetic dental implant structure, a dental structure, an orthopedic structure or an orthopedic implant, such characteristics may indicate the health of the object, or the health of the underlying foundation to which the object may be anchored or attached. The health of the object and/or the underlying foundation may also be correlated to densities or bone densities or a level of osseointegration; any defects, inherent or otherwise; or cracks, fractures, microfractures, microcracks; loss of cement seal; cement failure; bond failure; microleakage; lesion; decay or combinations thereof. For objects in general, for example, polymeric composite structures including honeycombs or layered honeycombs or metallic composite structure; an airplane structure, an automobile, a ship, a bridge, a building, industrial structures including, but not limited to power generation facilities, arch structures, or other similar physical structures; such measurements may also be correlated to any structural integrity, or structural stability, such as defects or cracks, even hairline fractures or microcracks, and so on.

For example, in measuring the damping characteristics of teeth, whether natural or restored, dental implant structures, orthopedic implant structures, and a variety of other applications where the measurement of damping characteristics is utilized, including, but are not limited to, testing airplane structures, composite structures, engineering materials, or the secureness of medical implants, and is particularly advantageous in locations that were difficult to access or where liquid couplants could not be used. Structural integrity, such as the looseness of a screw, cracks in teeth as well as bone and bone voids, debonded restorations, and damage in integrated circuit materials. However, the above list is not intended to be exhaustive.

The present invention provides an effective and repeatable measurement of the structural characteristics of an object, mentioned above. The object may be subjected to an energy application processes provided via a handpiece which forms a part of a computerized system capable of collecting and analyzing any data animating from the object. As noted above, many different structural characteristics may be determined using the system and methods of the present invention, including vibration damping capacities, acoustic damping capacities, structural integrity or structural stability of both mechanical and anatomical objects and any foundations they may be anchored thereon, as noted above. For an anatomical object, such as a tooth, natural or restored, prosthetic dental implant structure, a dental structure, or an orthopedic implant, examples of the structural characteristics as defined herein may include vibration damping capacities, acoustic damping capacities, or structural stabilities and may indicate the health of the object. The health of the object, may also be correlated to bone densities or a level of osseointegration; structural integrity such as defects or cracks, noted above. For objects in general, such measurements may also be correlated to their structural integrity such as defects or cracks, also a noted above. For a physical structure, such as a plane, an automobile, a ship, a bridge, a building or other similar physical structures or damping material suitable to aid in the construction of such structures, examples of the structural characteristics as defined herein may include vibration damping capacities, acoustic damping capacities, or structural stabilities and may indicate the health of the structural integrity of the object.

The instrument of the present invention may be used to such purposes and may be useful to predict the suitability of a material prior to construction in addition to detection of loss of cement seal; cement failure; bond failure; microleakage; decay and so on after the construction, as mentioned above. In addition, the present invention is also useful in distinguishing between defects inherent in the material making up the structure or object, and cracks or fractures as discussed above due to trauma or wear or repeated loadings. Defects inherent in the bone or material construction of an implant, or a physical structure, for example, may include lesions in the bone, similar defects in the implant construction or polymer, polymer composites or alloys, any type of ceramics, or metallic composites or alloys.

Figure 5:
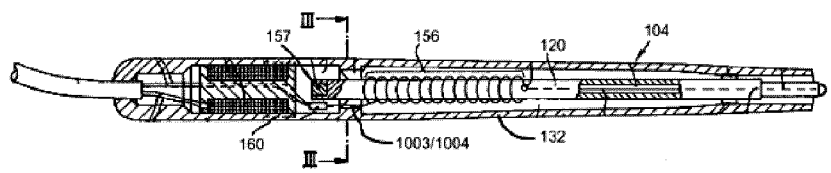
FIG. 5 illustrates a longitudinal cross-sectional view of an embodiment of a handpiece of the present invention.

In one embodiment, the handpiece 104 may be, for example, as exemplified in FIG. 1, in the form of a percussion instrument. The handpiece 104 may have a cylindrical housing 132 with an open end 132*a* and a closed end 132*b*. The open end 132*a* is tapered as exemplified here, though other configurations are also contemplated. An energy application tool 120, for example, a tapping rod 120, may be mounted inside the housing 132 for axial movement, as noted above. The handpiece also includes a drive mechanism 160, mounted inside the housing 132 for driving the tapping rod 120 axially within the housing 132 between a retracted position 128 and an extended position 129 during operation. In the extended position 129, the free end of the tapping rod 120 extends or protrudes from the open end 132*a* of the housing 132, as shown. The drive mechanism 160 may include an electromagnetic coil 156, as shown in FIG. 5, to be discussed further below. In one aspect, the tapping rod 120 may have a substantially constant cross-sectional construction over its entire length and has a permanent magnetic ensemble 157 mounted at the end away from the free end. The electromagnetic coil 156 of the drive mechanism 160 may be situated behind the other end of the tapping rod 120, resulting in a relatively small outside diameter for the handpiece 104.

Figure 6:
FIG. 6 illustrates a cross-sectional view taken along lines III-III of FIG. 5 of the present invention.

The mounting mechanism for the energy application tool 120, for example, tapping rod 120 may be formed by bearings 1003 and 1004, as shown in FIG. 6, for receiving or supporting the tapping rod 120 in a largely friction-free manner. In one example, the housing 132 may be about 150 mm long and about 15 mm thick. The magnetic or propulsion coil 156 may be situated in the housing 132 adjacent to the permanent magnet 157 and is axially behind the permanent magnet 157. The magnetic coil 156 and the permanent magnet 157 form a drive for the forward and return motion of the tapping rod 120. The drive coil 156 may be an integral component of the housing 130 and may be connected to a supply hose or line 1000.

The two bearings 1003 and 1004 may be substantially frictionless and may include, as shown in FIG. 6, a plurality of radially inwardly extending ridges separated by axial openings 1400. The axial openings 1400 of the bearing 1003 allow the movement of air between a chamber 1500 which is separated by the bearing 1003 from a chamber 1600, which chambers are formed between an inner wall surface of the housing 132 and the tapping rod 120. Air movement between these chambers 1500 and 1600 may thus compensate for movement of the tapping rod 120.

Figure 2A:
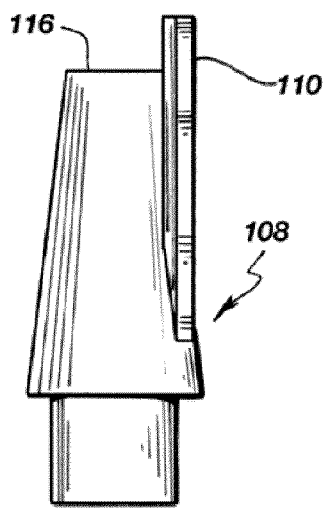
FIGS. 2a and 2f each illustrates a side perspective view of an embodiment of a sleeve and tab of the present invention.
Figure 26:
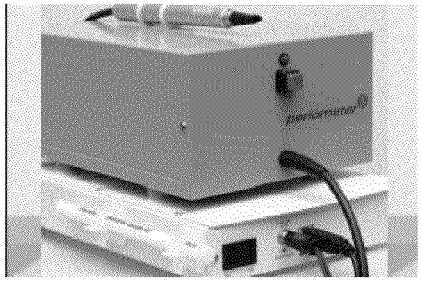
FIG. 26 shows a picture of an embodiment of the system of the present invention.
Figure 26A:
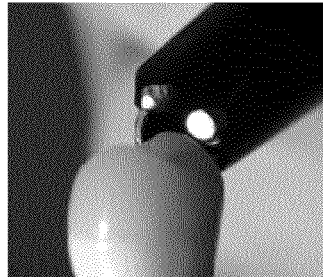
FIGS. 26a-b show the measuring device of the system of the present invention.

Referring again to FIG. 1, a sleeve 108 is positioned towards the end 132*a* and extending beyond it. The sleeve 108 envelops the end of the housing 132*a* and is flattened at its end 116 for ease of positioning against a surface of an object 112 during operation. The sleeve 108 has a tab 110, as shown in FIGS. 2*a* and 2*f*, protruding from a portion of its end 116, so that when the open end 116 of the sleeve 108 is in contact with a surface of the object 112 undergoing the measurement, the tab 110 may be resting on a portion of the top of the object 112, as shown here in the FIGs.6, 26*a* and 26*b*. The tab 110 and the sleeve 108 may both assist in the repeatable positioning of the handpiece 104 with respect to the object 112 and the tab 110 may be placed substantially at the same distance from the top of the object 112 every time for better reproducibility. This can be seen better in FIGS. 2b, 2c, 2d, 2g, 2h and 2i, FIGS. 7a-d, or FIGS. 26a and b, though the object 112 is not specifically shown in FIGS. 2b-d or 2g-2i. As noted above, the object may include an anatomical structure or a physical or industrial structure, though an anatomical structure is shown in the figures mentioned here.

Figure 2B:
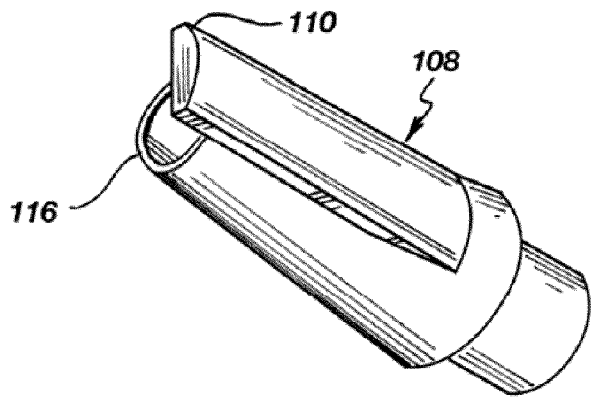
FIGS. 2b and 2g each illustrates an end perspective view of an embodiment of a sleeve and tab of the present invention.
Figure 2C:
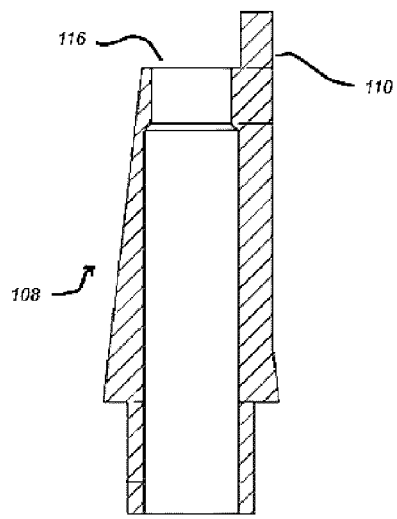
FIGS. 2c and 2h each illustrates a perspective cross-sectional view of an embodiment of a sleeve and tab of the present invention.
Figure 2D:
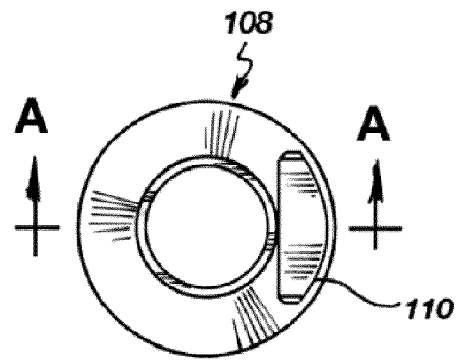
FIGS. 2d and 2i each illustrates an end cross-sectional view of an embodiment of a sleeve and tab of the present invention.
Figure 2E:
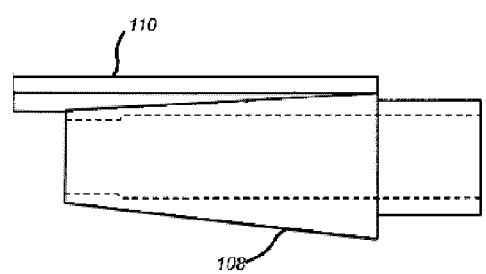
Figure 2F:
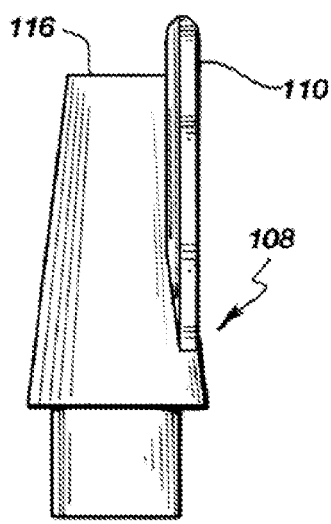
Figure 2G:
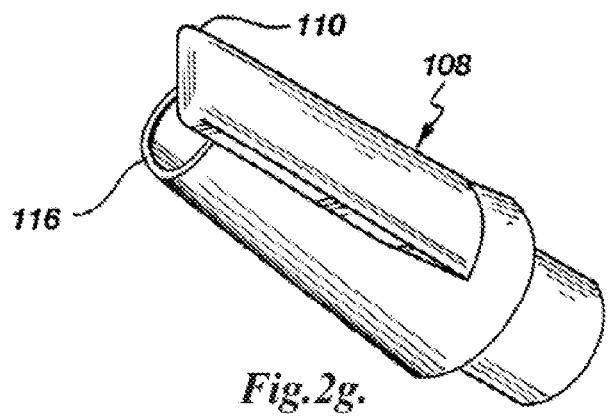
Figure 2H:
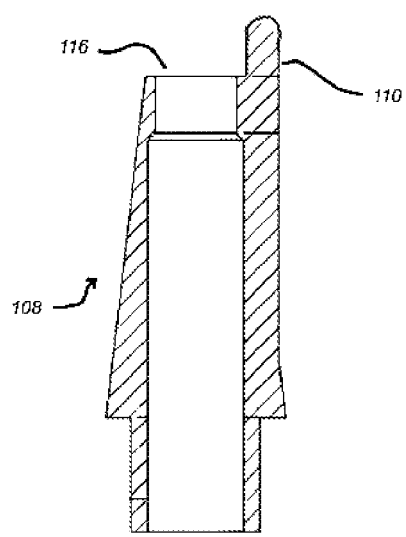
Figure 2I:
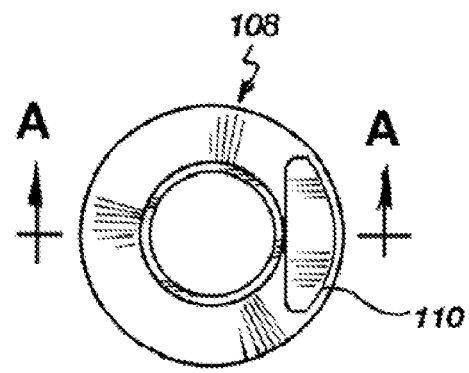
Figure 2J:
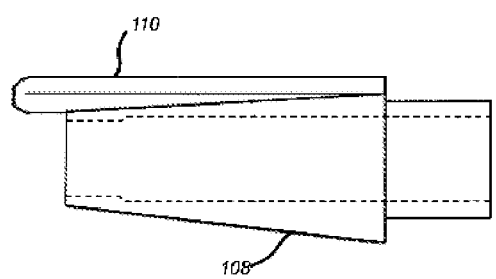
Figure 26B:

The end 116 of the sleeve 108 not having the tab 110 protruding from it is flat or substantially flat, as shown in FIGS. 1, 2a, 2b, 2c, 2f, 2g, 2h and 26b, and the part of the tab 110 in contact with the top of the object 112 is also flat or substantially flat, as shown in FIGS. 2a, 2b, 2c , 2f, 2g, 2h and 26b. The tab 110 may extend in a substantially parallel direction from the end of the sleeve 108, as shown in FIGS. 2a, 2b, 2c , 2f, 2g, 2h and 29b. In one aspect, the tab 110 may be integral with the sleeve 108 for a distance before protruding from the end of the sleeve 108, as shown in FIGS. 2b and 2g, keeping substantially the cross-sectional outline of the sleeve 108, before and after protruding from the end 116 of the sleeve 109. In this embodiment, the protruding portion of the tab 110 may have an arched top portion, as shown in FIGS. 2b and 2g. In another aspect, the tab 110 may protrude from the top of the sleeve 108, not keeping the cross-sectional outline of the sleeve 108, before and after protruding from the end 116 of the sleeve 108, as shown in FIGS. 2a, 2c, 2f and 2h. In this embodiment, the protruding portion of the tab 110 may have a rectangular cross-section, as shown in FIGS. 2c 2h and 26b. In any of the embodiments, the corners of the tabs 110 are smooth or rounded or substantially smooth or rounded to avoid any catching on the object 112 they may be resting on, as shown in FIG. 1 a. In other embodiments, the tab 110 may be smooth, though the corners may not necessarily be rounded, as shown in FIG. lb. In a further embodiment, as shown in the cross-sectional FIGS. 2d and 2i, the cross-section of the tab 110 does not extend outside the peripheral of the cross-section of the sleeve 108.

Figure 3:
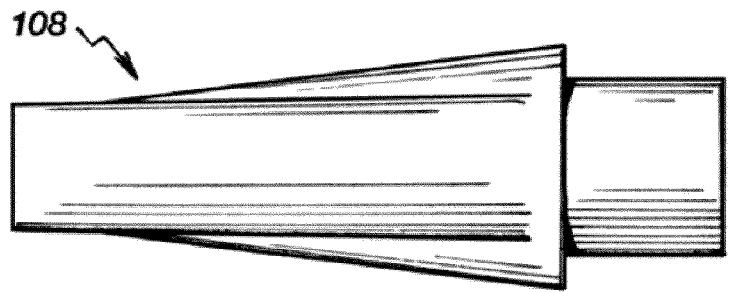
FIG. 3 shows a perspective side view of an embodiment of a sleeve of the present invention.
Figure 3A:
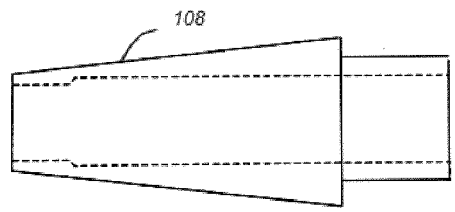
FIG. 3a shows a side view of the embodiment of a sleeve of FIG. 3.
Figure 3D:
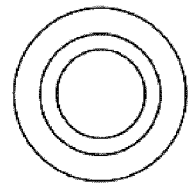
FIG. 3d shows a cross-sectional view of the sleeve of FIG. 3a viewed from the end of the sleeve to be attached to the handpiece.

FIGS. 3 and 3a show a perspective side and side view of an embodiment of a sleeve 108 of the present invention. In this embodiment, the sleeve 108 is tapered towards the free end 116 with a threaded portion 116a for attachment to the open end of the housing 132a. FIG. 3d shows a cross-sectional view of the sleeve of FIG. 3a viewed from the end of the sleeve to be attached to the handpiece 104.

Figure 3B:
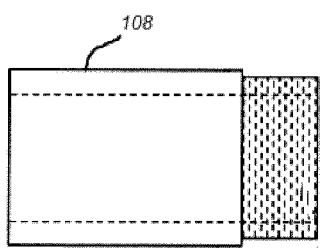
FIG. 3b shows a side view of another embodiment of a sleeve of the present invention.
Figure 3C:
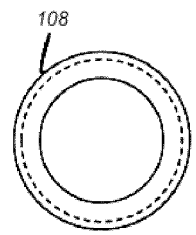
FIG. 3c shows cross-sectional view of the sleeve of FIG. 3b viewed from the end of the sleeve.

In another embodiment, the sleeve 108 may be substantially non-taper, as shown in FIG. 3b. In this embodiment, the cross-section of the end of the sleeve 108 is substantially round, as shown in FIG. 3c.

In these embodiments, the sleeve 108 may be attached to the handpiece 104 by means of threads 116a. The threaded portion 116a may have a dimension that allows for secured attachment.

Figure 4A:
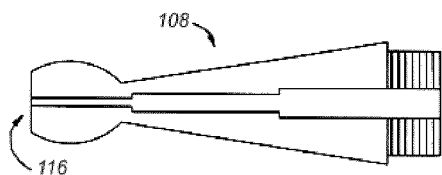
FIGS. 4a-b illustrate embodiments of the sleeve of the handpiece of the present invention.
Figure 4B:
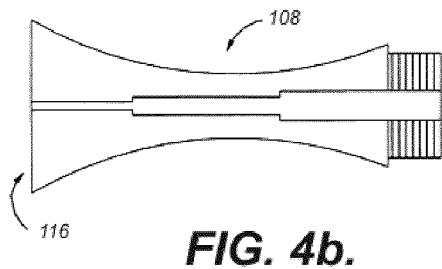

In FIGS. 4a-b, other embodiments of the sleeve 108 of the handpiece 104 are shown. In FIGS. 4a and 4b, a polymer sleeves 108 features flattened tips 116 approximately orthogonal to the object 112 surface to further assist with the alignment of the handpiece 104. In FIG. 4b, the outer diameter is at least several times larger than the inner diameter of the sleeve 108. Other shapes and configuration of the sleeve 108 may be possible, so long as the shape or form used assists with the approximately orthogonal alignment of the handpiece 104 and attenuated vibrations from the object 112 caused by the measurement procedure that might travel through the sleeve 108 and into the housing 132 of the handpiece 104 where sensitive measurements are being taken.

Figure 7C:
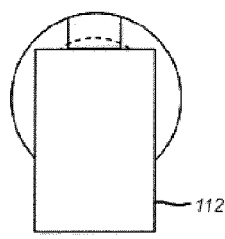
FIG. 7a illustrates a side view of an embodiment of the sleeve and tab of any of FIGS. 2a-d when positioned on an object.
FIGS. 7b and c illustrate embodiments of a top view and front view, respectively, of embodiments of a sleeve and tab of the present invention during operation.
Figure 7A:
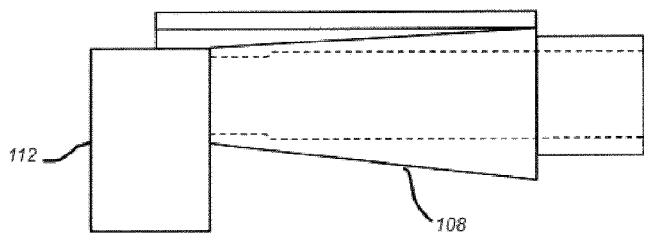
Figure 7B:
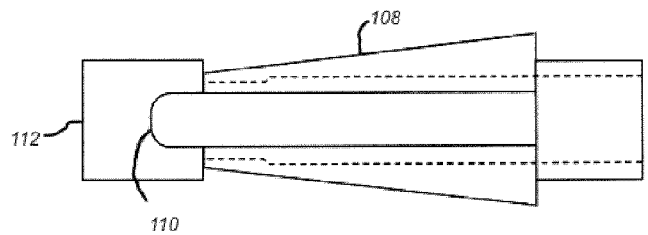

FIG. 7a illustrates a side view of the sleeve 108 and tab 110 of any of the embodiments of FIGS. 1a-b and 2a-2d when positioned on an object 112 during operation. The sleeve 108 touches an object 112, such as a tooth, while the tab 110 rests on the top of the tooth 112, as shown in FIGS. 7b and c. The surface of the tab 110 in contact with the object 112 may be contoured to be better positioned on the top of a tooth 112 or it may be flat. FIGS. 7b and c illustrate embodiments of a top view and a front view, respectively of embodiments of a sleeve and tab of FIGS. 1a and 1b during operation, respectively.

Figure 8:
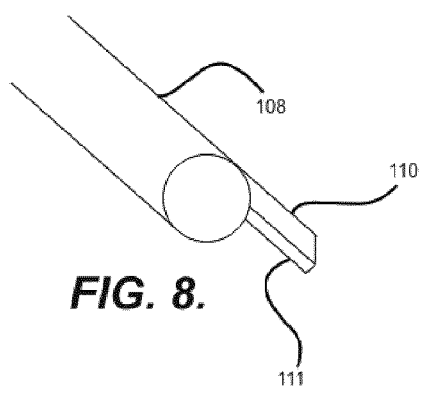
FIG. 8 illustrates another embodiment of the sleeve and tab of the present invention.
Figure 8B:
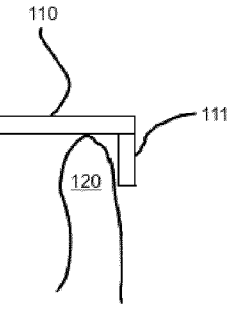
FIGS. 8a and 8b illustrate the sleeve and tab embodiment of FIG. 8 during operation.
Figure 8A:
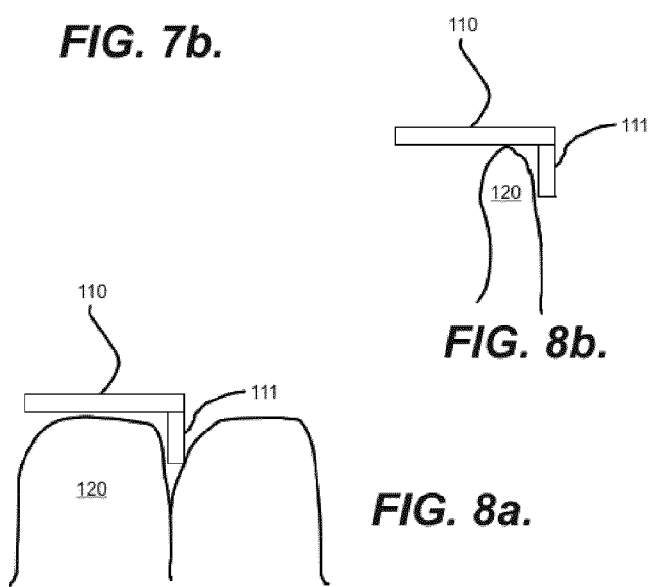

In other embodiments, the sleeve 108 may include a feature 111, for example, a ridge, protrusion or other similar features substantially orthogonal to the surface of the tab 110 on the side facing the surface of the object 112, as shown in FIG. 8. For example, for teeth, the ridge or protrusion may nest between adjacent teeth and may thus aid in preventing any substantial lateral movement of the tab 110 across the surface of the object 112, as shown in FIG. 8a or resting on an orthogonal surface, such as the inside surface of the tooth to be tested, as shown in FIG. 8b. The sleeve 108 having a tab 110 and feature 111 may further aid in the repeatability of positioning the energy applying tool such as the tapping rod 120 on the object 112. For the embodiment of 8a, the tab 110 may extend from the sleeve at a sufficient length to enable the ridge or protrusion 111 to rest properly between the adjacent teeth. For the embodiment of 8b, the tab 110 may be of a sufficient width to enable the ridge or protrusion 111 to rest properly on the inside surface of the tooth to be tested.

In one aspect, for example, if the object 112 is teeth, the feature 111 may be short and of a sufficiently small thickness so that it may fit between adjacent teeth 112. In another aspect, for example, if the object 112 is a tooth, the feature 111 may be short and shaped to fit between the top portions of adjacent teeth 112. In yet another aspect, for example, if the object 112 is a tooth, and the feature 111 is to rest against the back surface, it may be of a dimension to cover a major portion of the back surface.

For other objects 112, the feature 111 may be shaped accordingly or of a dimension suitable for the object 112.

To facilitate the operation of the handpiece 104, the sleeve 108 may be made of any material having vibration attenuating properties and may be of such length so that any vibration traveling through the sleeve 108 to the housing 132 of the handpiece 104 may be attenuated. In one embodiment, the sleeve 108 and/or the tab 110, and the end of the housing 132b the sleeve 108 is attached to may be made of the same material. In another embodiment, the sleeve 108, and/or the tab 110, and the end of the housing 132b the sleeve 108 is attached to may be made of materials having similar vibration attenuating properties. In yet another embodiment, the sleeve 108 and/or the tab 110 and the end of the housing 132b the sleeve 108 is attached to may be made of different materials, for example, the housing 132 may be made of metal or composite, while the sleeve 108 and/or tab 110 may be made of a polymer or composite. In a further embodiment, the sleeve 108 and/or tab 110 and the end of the housing 132b the sleeve 108 is attached to may be made of materials having different vibration attenuating or damping properties. In any of the embodiments mentioned above, the feature 111, whether it is a protrusion, a ridge or other similar features or features having similar functionalities, if present, may also be made of same materials as the sleeve 108.

In general, it may be desirable for the sleeve 108 to have sufficient rigidity such that it may consistently fit over or into a handpiece housing 132 and may not collapse during use. If multiple uses are contemplated, the sleeve 108 may generally be constructed to withstand multiple sterilization procedures, such as by autoclave, if desired. In other embodiments, the sleeve 108 may be disposable and thus may be constructed of any material that may be formed into a sleeve 108. Examples of appropriate materials may include, but are not limited to, for example, a polymer that may be molded, thermoformed or cast. Suitable polymers include polyethylene; polypropylene; polybutylene; polystyrene; polyester; polytetrafluoroethylene (PTFE); acrylic polymers; polyvinylchloride; Acetal polymers such as polyoxymethylene or Delrin (available from DuPont Company); natural or synthetic rubber; polyamide, or other high temperature polymers such as polyetherimide like ULTEM®, a polymeric alloy such as Xenoy® resin, which is a composite of polycarbonate and polybutyleneterephthalate, Lexan® plastic, which is a copolymer of polycarbonate and isophthalate terephthalate resorcinol resin (all available from GE Plastics); liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797,198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof. Some of these materials are recyclable or be made to be recyclable. Compostable or biodegradable materials may also be used and may include any biodegradable or biocompostable polyesters such as a polylactic acid resin (comprising L-lactic acid and D-lactic acid) and polyglycolic acid (PGA), polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers, and polyester/urethane resin. Some non-compostable or non-biodegradable materials may also be made compostable or biodegradable by the addition of certain additives, for example, any oxo-biodegradable additive such as D2W™ supplied by (Symphony Environmental, Borehamwood, United Kingdom) and TDPA® manufactured by EPI Environmental Products Inc. Vancouver, British Columbia, Canada.

In addition, any polymeric composite such as engineering prepregs or composites, which are polymers filled with pigments, carbon particles, silica, glass fibers, or mixtures thereof may also be used. For example, a blend of polycarbonate and ABS (Acrylonitrile Butadiene Styrene) may be used for the housing 132 and sleeve 108. For further example, carbon-fiber and/or glass-fiber reinforced plastic may also be used.

Synthetic rubbers may be, for example, elastomeric materials and may include, but not limited to, various copolymers or block copolymers (Kratons®) available from Kraton; Polymers such as styrene-butadiene rubber or styrene isoprene rubber, EPDM (ethylene propylene diene monomer) rubber, nitrile (acrylonitrile butadiene) rubber, and the like.

In some embodiments, the sleeve 108 and/or housing 132 may also be made of metallic and/or ceramic material(s) which may further be coated and/or treated with a suitable material, such as a polymer or composite as above. For example, a metallic and/or ceramic material may be utilized that may be substantially vibration dampening/absorbing/reflecting. A visco-elastic and/or other coating may also be employed such that vibrations and/or other mechanical energy may not translate into metallic and/or ceramic components of the sleeve 108 and/or housing 132.

In one embodiment, titanium may be used for the sleeve 108 and/or housing 132, or components/portions thereof.

In another embodiment, piezoelectric materials, such as piezoelectric ceramics, may be utilized. Piezoelectric materials may generally be utilized to convert mechanical energy into electrical energy.

In one specific embodiment of the invention, the polymer sleeve 108 of the handpiece 104 extends out so that the distance from the tip 116 of the polymer sleeve 108 in contact with the specimen 112 to the head 128 of the tapping rod 120 in its retracted stationary position ranges generally from, for example, about 3.5 millimeters to about 5.5 millimeters, and more for example, about 3.75 millimeters to about 4.5 millimeters. In one exemplary embodiment, the distance from the tip 116 of the polymer sleeve 108 of the handpiece 104 in contact with the specimen 112 to the head 128 of the tapping rod 120 in its retracted stationary position may be about 4 millimeters. These measurements of the tapping rod 120 are simply exemplary and are not limiting. The polymer sleeve 108 length in one embodiment is dependent upon the length of the tapping rod 120 and the total distance that the tapping rod 120 can travel when activated without a significant degradation in forward progress due to friction and gravity.

As noted above, the sleeve 108 may be removable and may be attached to the housing 132 in any threaded attachment, friction fit, mating bayonet formations, tongue and groove type formations, snap fit, internesting pin and pinhole formations, latches and other interconnecting structures. In one exemplary embodiment, the sleeve and the housing may be a custom-made threaded system for better fit.

In one exemplary embodiment, the other end 136 of the polymer sleeve 108 may be threaded 116a so that it connects to the handpiece housing 132 with a similar threading, as illustrated in FIG. 3. The plane including the specimen end 116 of the polymer sleeve 108 is approximately orthogonal to the axis of the handpiece housing. Also, the surface area of the specimen end 116 of the polymer sleeve 108 may be sufficiently large. This and the tab 110 assist in the approximately orthogonal placement and position stability of the handpiece 104. In one embodiment, the outer diameter of the specimen end of the tip 116 is generally within the range of, for example, from about 6 millimeters to about 14 millimeters, and more for example, within the range of from about 8 millimeters to about 11 millimeters. In one exemplary embodiment, the outer diameter is about 9.5 millimeters. The inner diameter of the specimen end of the tip 116 is generally within the range of, for example, from about 3 millimeters to about 6 millimeters, and more for example, within the range of from about 4 millimeters to about 5 millimeters. In one exemplary embodiment, the inner diameter is about 4.7 millimeters.

The sleeve may also have varying inner diameters which decreases from where the sleeve is threaded 136 to the specimen end 116 of the sleeve 108. FIG. 1 shows one embodiment where the polymer sleeve 108 has three discrete inner diameters. Other embodiments have more or less than three inner diameters, with one embodiment having a continuously, decreasing inner diameter from where the polymer sleeve was threaded 136 to the specimen end 116 of the polymer sleeve 108. Decreasing inner diameters may help guide the tapping rod 120 to strike the specimen 112 in a consistent location and at a consistent angle of inclination. The sleeve 108 with the tab 110 may provide greater accuracy and precision of positioning on an object 112. For example, a polymeric sleeve 108 having a damping capacity and of such length so as to attenuate any stress waves that might interfere with the measurement procedure enables the tip 116 of the polymer sleeve 108 to be placed directly against the object 112 during operation. By placing the tip 116 of the polymer sleeve 108 of the handpiece 104 directly against the object 112 has the advantage of keeping the distance between the object 112 and the tip 116 of the sleeve 108 of the handpiece 104 and the positioning of the tip 116 of the sleeve and a surface of the object 112 to be anchored further by the tab 110, and feature 111, if present, be substantially consistently the same, resulting in better data reproducibility and greater accuracy. This capability eliminates the guessing of distance and positioning and eliminates errors due to, for example, the patient's head or the operator's hand shaking ever so slightly during the measurements.

In one embodiment of the present invention, the tip 116 of the sleeve 108 with the tab 110 of the handpiece 104 is positioned directly on the specimen 112 to provide the capability of recreating consistent and accurate measurements essentially independent of the evaluations of the operator and the slight movements in the specimen 112, if present.

In another embodiment, Also, the tip 116 of the sleeve 108 with the tab 110 and feature 111 of the handpiece 104 is positioned directly on the specimen 112 to provide the capability of recreating consistent and accurate measurements essentially independent of the evaluations of the operator and the slight movements in the specimen 112, if present.

Further, the resting of tip 116 and the tab 110, or the tab 110 and feature 111 of the sleeve 108 directly on the object 112 also make it easier for the operator to hold the handpiece 104 steady and to maintain a consistent distance between the tip 116 of the sleeve 108 and the object 112 while measurements are being made. The sleeve 108 which has a flattened tip 116, as shown in FIG. 1, further assists in aligning of the handpiece 104 approximately orthogonal to the surface of the object 112 when the tip 116 is placed in contact with the object 112. Self-alignment through contact between the tip 116, the tab 120, and the object 112, or the tip 116, the tab 110 and feature 111, results in more accurate and precise measurements with the angle at which the tapping rod 120 strikes the object 112 being kept constant both during the measurements and in subsequent measurements.

In addition, the use of a polymer or other material having vibration attenuating properties for the sleeve 108 of the handpiece 104 may also result in a cleaner signal by keeping stress waves from propagating up the housing 132 of the handpiece 104. In one exemplary embodiment, PTFE may be used as the sleeve 108. In another embodiment, polyoxymethylene may be used for the sleeve 108. PTFE and polyoxymethylene may be autoclavable and of sufficiently high damping capacity to attenuate stress waves from the object 112. The sleeve 108 material may generally have a damping capacity as represented by its loss coefficient, ranging from about, for example, 0.03 to about 0.2, and more for example, within the range of from about 0.06 to about 0.1. In one exemplary embodiment, the loss coefficient may be about 0.08. PTFE also has the advantage of being a solid lubricant which reduces friction between the sleeve 108 and the tapping rod 120 as the tapping rod 120 travels back and forth during the measurement procedure.

With the flattened tip 116 and the tab 120 of the sleeve 108 which self-aligned itself with the object 112, the operator is aided in keeping the handpiece 104 approximately horizontal to the ground and approximately orthogonal to the surface of the object 112 undergoing measurement. The handpiece 104 may also have a level indicator 140 attached to the housing 132 of the handpiece 104 to further assist the operator in holding the handpiece 104 approximately horizontal during testing. In one embodiment of the present invention, the level indicator 140 may include an air bubble 144 trapped in a liquid held in a transparent casing. The user simply keeps the air bubble 144 centered between two marks 148 and 152 in the middle of the transparent casing to assure that the handpiece 104 is in an approximately horizontal position.

Figure 1A:
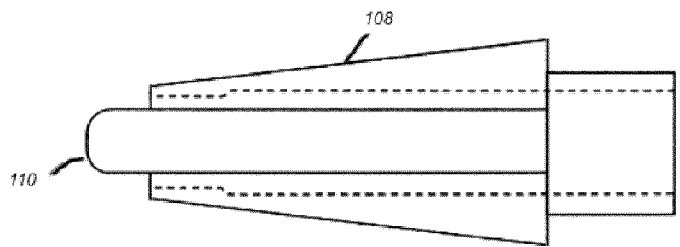
FIGS. 1a and 1b show illustrative embodiments of the tab of the present invention.
Figure 1B:
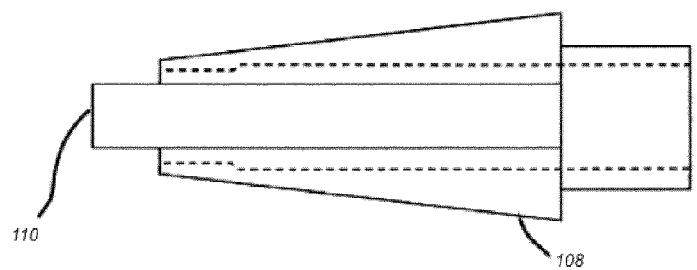

Returning again to FIG. 1, the handpiece may be part of a system including a drive mechanism 160 that may include an piezoelectric force sensor 160a, a system hardware 164, for example, a computer 164 having high speed data acquisition capability that may be effected by a high speed data acquisition board. In one embodiment, a sixteen bit analog-to-digital channel on a data acquisition card housed in the computer 164 may be used. In another embodiment, a purely digital channel may be used. In FIG. 1a, the drive mechanism 160 may include a linear variable differential transformer 160b for sensing and measuring the displacement of the energy application tool such as the tapping rod 120, as shown in FIGS. 1 and 1a, before, during and after the application of energy. The linear variable differential transformer 160b may be a non-contact linear sensor. The sensor may utilize inductive technology and thus capable of sensing any metal target.

In one embodiment, the energy application process of the handpiece 104 may be triggered via a mechanical mechanism, such as by a switch mechanism 140, for example, as shown in FIG. 1, a finger switch located at a convenient location on the handpiece for easy activation by the operator.

In another embodiment, the energy application process of the handpiece 104 may be triggered via a foot control.

In a further embodiment, the energy application process of the handpiece 104 may be triggered, for example, via voice control. The voice control may be coupled to an electrical control device. The electrical control device may include a microprocessor and a switch such as an electromechanical switch or a solid state switch. An electronic voice control circuit technology, similar to the technology used in electronic devices such as toys, cell phones, automobiles and other consumer electronics, may be used to activate the energy application process. In a still further embodiment, the energy application process of the handpiece 104 may be triggered via remote wireless control. The remote wireless control may be coupled to the switch mechanism 140 which may include a microprocessor and a switch such as an electromechanical switch or a solid state switch. The switch may be activated through infrared radiation or through wireless radio signals or through light from the visible portion of the electromagnetic spectrum.

In one exemplary embodiment, to commence the testing of an object 112, the tip 116 of the sleeve 108 of the handpiece 104 is placed against the specimen 112 and the tapping rod 120 inside the handpiece 104 is activated with the push of a finger switch 124 located on the handpiece 104, as shown in FIG. 1.

Upon activation of the finger switch 124 or other switches on the handpiece 104, a foot control, voice or wireless control, a movable tapping rod 120 is driven by a propulsion coil 156 through an orifice in the sleeve 108 to impact the object 112, for example, sixteen times in four seconds. As the tapping rod 120 moves, a magnet 157 located on the tapping rod 120 is displaced with respect to a measuring coil 158. The acceleration of the tapping rod 120 may be measured by an piezoelectric force sensor 160a, or the displacement of the tapping rod 120 may be sensed and measured by the linear variable differential transformer 160b. During operation, after application of energy, such as tapping with the tapping rod, when the measurement is being made by the piezoelectric force sensor

160a, signals corresponding to the shock wave resulting from such impact are collected and sent to the computer 164, as shown in FIG. 1. In one embodiment, a piezoelectric force sensor 160a may be used to produce signals corresponding to the shock wave resulting from each impact. In one aspect, a sixteen bit analog-to-digital converter channel on a data acquisition card housed in a computer 164 may be used. In such embodiments, the computer 164 operates at a sampling rate of at least about 800 kHz; although in other embodiments, the computer 116 may operate at a sampling rate of at least about 600 kHz; more for example, a sampling rate of at least about 500 kHz may be used. The signals generated by the piezoelectric force sensor 160a may be provided to a data acquisition board housed in the computer 164 via any instrumentation interface. In one aspect, the signals may be transmitted from the piezoelectric force sensor 160a to the computer 164 via a coaxial cable 168 to the high speed data acquisition card. In another aspect, the instrumentation interface may include a signal conditioner and an independent power supply. In yet another aspect, a modified embodiment of the instrumentation interface may be incorporated within the computer 164.

Software stored in the computer 164 acquires and analyzes, for example, ten of the sixteen impacts to quantitatively determine the structural characteristics, for example, damping capacity or other above listed characteristics of the object 112 or its surrounding or foundation to which it is attached. Typically, six to ten impacts are sufficiently adequate for sampling of the loss coefficient for a given object, for example. For example, in one embodiment, the tapping rod 120 impacts the object 112 approximately sixteen times in a period of four seconds. In other embodiments, faster or slower impact repetition rates are used. In an exemplary embodiment, the tapping rod 120 is driven by one or more propulsion coils 156 electronically activated by a finger switch (not shown), although the propulsion coils 156 can be activated remotely in other embodiments, as noted above.

When the tapping rod 120 impacts the object 112, some of the kinetic energy of the tapping rod 120 is converted to mechanical energy propagating through the object 112 as a stress wave. Most of the remaining of the kinetic energy is converted (dissipated) to heat, as dictated by the loss coefficient and structure of the object 112. A portion of the propagated mechanical energy is reflected back to the tapping rod 120, where it can be detected by a piezoelectric force sensor 160a mounted within the housing 106. The piezoelectric force sensor 160a produces signals that correspond to the reflected mechanical energy resulting from the impact between the tapping rod 120 and the object 112.

In an illustrated embodiment, the computer 164 may include virtual instrumentation software capable of analyzing the signals received from the piezoelectric force sensor 160a. A wide variety of different types of data acquisition software can be used to acquire data from the piezoelectric force sensor 160a. In one embodiment, customized data acquisition software developed using the LabVIEW programming environment, available from National Instruments (Austin, Tex.), may be used, although other programming environments can be used in other embodiments.

After the signals are received from the piezoelectric force sensor 160a, the data processing software is capable of quantitatively measuring the characteristics desired, for example, damping capacity of the object 112, which may often be expressed in terms of the loss coefficient 17. For a series of impacts, as described above, several calculations of the damping capacity may be performed. For example, in one embodiment the tapping rod 120 impacts the object 112 sixteen times, and the damping capacity of the object 112 may be calculated for ten of the sixteen impacts. In such embodiments, the standard deviation of the damping capacity measurements can be calculated, thereby providing the user with an indication of the accuracy of the measurements. Specifically, if the handpiece 104 is not properly aligned with the object 112, or if another source of error is introduced into the measurement process, this error will likely manifest itself in the form of a elevated standard deviation of a series of damping capacity measurements. The various embodiments of any part of the system, such as the sleeve with the tab and/or feature discussed above may be used in making any testing or measurement of any structural characteristics of any of the objects previously discussed.

As noted above, the present invention has applications also in the detection of internal damage such as microcracking, fracture, microfracture and delamination in composite structures and other engineering materials. Composites are generally more susceptible to damage development than unreinforced metals, particularly when they are under stresses that approach the tensile strength of the material. The present invention is useful for detecting damage through nondestructive testing in composite materials and structures.

Figure 9:
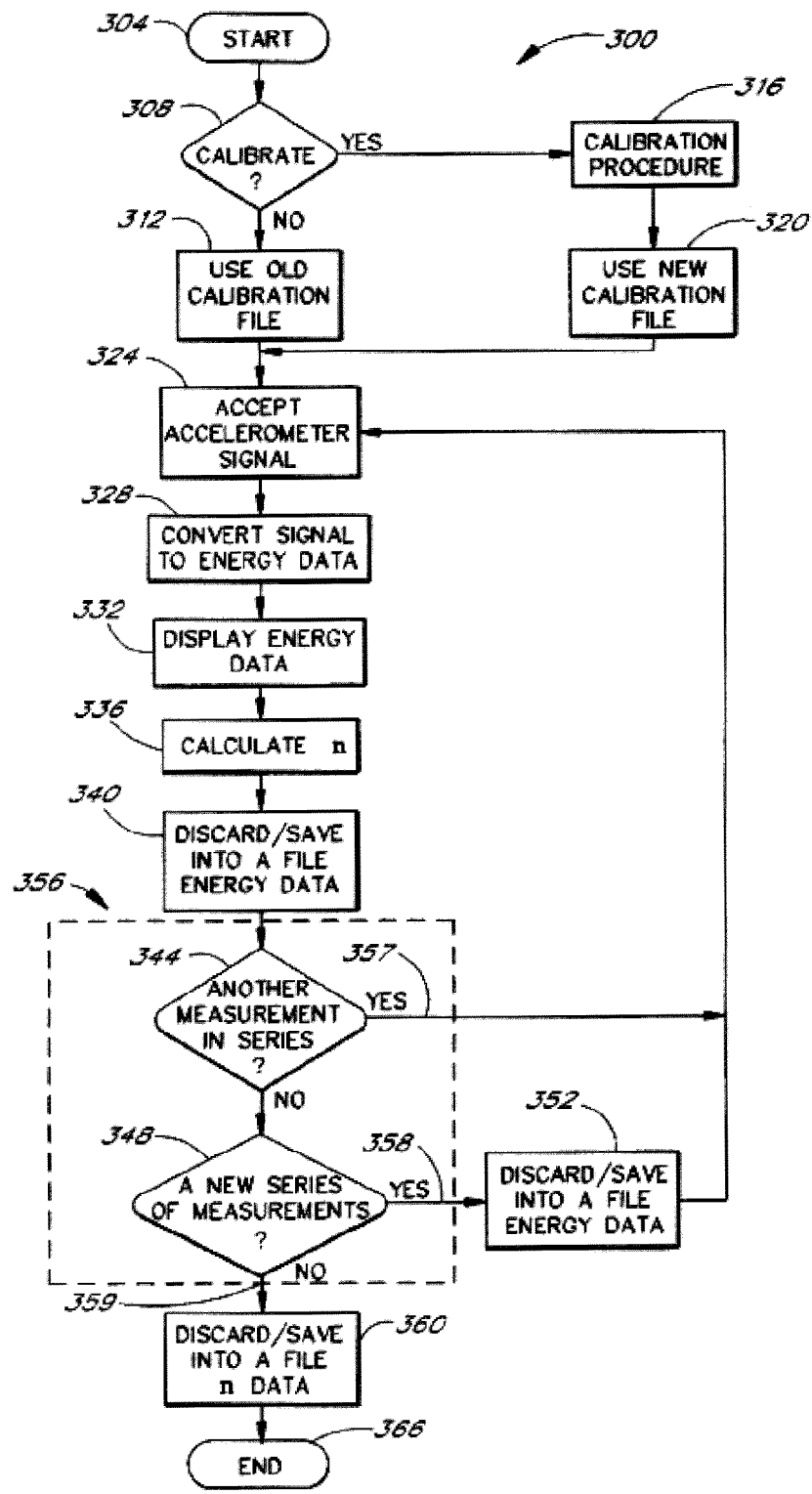
FIG. 9 illustrates a flow chart of a software program in an embodiment of the invention.

FIG. 9 shows a flowchart 300 of one exemplary embodiment of software procedure. After the program is loaded and executed 304, the next step 308 determines whether calibration is needed. If a familiar testing configuration is to be implemented, then the program loads previously determined calibration values stored in a file 312. A calibration file can be chosen from among the many previous calibration files stored in memory. If a new testing configuration is being used, then a calibration procedure 316 was completed and the new calibration values stored in a new file before the new calibration values are implemented at step 320. In the next step 324, the program accepts the signal from the piezoelectric force sensor 324, converted the signal into energy data 328, displaying the energy data in graphical and textual form on the computer monitor 332, calculating n, for example, the loss coefficient, .eta. 336; and/or calculate standard deviation of the loss coefficient measurements and Normalized Ideal Fit Error; and then either discarding or saving into a file the energy data depending upon the discretion of the operator 340.

Then, the operator chooses from among three options: make more measurements in that series of measurements 357; commence a new series of measurements 358, or exit the program 359. In one embodiment of the program, a graphical user interface displays the above three options from which the operator could choose. This interface is reflected by the box 356 outlined in the flowchart 300 which has three paths leading out of the box 357, 358 and 359.

If more measurements in the series of measurements are requested 357, the program loops back to the step where the program accepted the signal from the piezoelectric force sensor 324. If more measurements in the series of measurements are not requested, but instead a new series of measurements are requested, then program either discards or saves into a file the energy data depending upon the discretion of the operator 352 before looping back to the step where the program accepted the signal from the piezoelectric force sensor 324. If more measurements in the series of measurements are not requested and no new series of measurements are requested 359, then the program is either discarded or saved into a file the loss coefficient data depending upon the discretion of the operator 360 before ending the program 366.

Also, the mechanical energy associated with an impact against a natural tooth, for example, is primarily dissipated by the periodontal ligament. More specifically, when a tooth is subjected to an impact force, a stress wave is transmitted through the tooth and into the periodontal ligament, which functions to connect the tooth to the underlying bone. Because of the way it deforms, the periodontal ligament acts as a shock absorber, dissipating much of the energy associated with the impact. This damping process advantageously reduces the resultant impact force transmitted to the surrounding bone. In contrast, dental implant prostheses often have no mechanism by which to dissipate significant amounts of mechanical energy because of the nature of the materials used. Thus, mechanical energy tends to pass from an implant structure to the underlying bone with relatively little damping. This difference in mechanical behavior may be particularly critical for people who habitually brux and/or clench their teeth, since such behavior imparts relatively large impact forces on teeth. For a physical structure, whether or not a damping material is incorporated into the structure, the mechanical energy associated with an impact against the structure may generate a different response when there is a crack, microcrack, fracture, microfracture, delamination, defect or any structural instability than for a structure without a crack, microcrack, fracture, defect or any structural instability.

The relative extent to which a material dissipates elastic mechanical energy can be characterized using the loss coefficient, as discussed previously. Loss coefficient values may be determined for any of the objects mentioned above, including natural teeth, as well as for a wide variety of implant-supported superstructures, such as superstructures made of resin matrix composites, gold alloys, porcelain fused to gold laminates, all ceramic restorations or any other material suitable for use in the oral cavity. Implant-supported structures typically dissipate less mechanical energy than their natural tooth counterparts. However, the ability of an implant to dissipate mechanical energy depends on the level of osseointegration around the implant: poor osseointegration between an implant and the surrounding bone can cause abnormally high levels of energy dissipation. Thus, energy dissipation initially increases after placing an implant, for example, due to bone remodeling but then usually decreases as osseointegration progresses. Eventually, the energy dissipation (damping) capacity of the implant becomes constant as the osseointegration process progresses to completion. As noted above, for normal healthy teeth, the percussive energy generated by mastication is attenuated by the periodontal ligament at the healthy bone-natural tooth interface. When a natural tooth is damaged or diseased, an implant replaces it, but probably and may be definitely, without the ligament as it is generally lost. In most cases, in a successfully integrated implant, there is no ligament. Under this, the implant may transmit the percussive forces directly into the bone. To compensate for this loss, the use of, for example, some composites, zirconia and so on, to fabricate the implant abutment has been shown to be effective in numerous studies. The instrument of the present invention may serve in aiding in the construction or fabrication of and/or selection of a material for an anatomical structure, for example, an implant. The measurement of the dynamic response to load of said abutment materials may be used to such purposes and may be useful to predict the suitability of the restorative material for the implant prior to implantation or prior to restoration.

Since buccal loading is the more dangerous type of stress encountered, the ability to correlate test results with actual response when implanted is another aspect of the present invention. In general, occlusal clenching induces relatively low stresses, working and/or nonworking motion may produce side loading and may induce much higher stresses which may generate highest stress concentration at internal surface and below the cemental enamel margin. Thus, quantitative percussion diagnostics, using the system of the present invention may aid in selecting the best material or construction design in or for an implant.

The loss coefficient determination may be performed according to that described in U.S. Pat. No. 6,120,466, the contents of which are hereby incorporated by reference in its entirety. FIGS. 14 and 15 show formulae used for calculating loss coefficient and 16a show an example of a loss coefficient measurement.

Other determinations, such as measuring, for a time interval, energy reflected from the object as a result of the tapping or applying energy, which may include creating a time-energy profile based on the energy reflected from the object during the time interval, and/or evaluating the time energy profile to determine the damping capacity of the object may be determined, such as disclosed in U.S. Pat. Nos. 6,997,887 and 7,008,385, the contents of all of which are hereby incorporated by reference in their entirety.

For example, as illustrated also in FIG. 1, the computer 164 may further include memory registers, such that time versus percussion response, for example, the amount of energy reflected from the object 112 at several points over a discrete time period can be recorded. In such embodiments, the energy returned from the object 112 can be plotted as a function of time on a display attached to the computer 164. This configuration allows the user to view and analyze the time-energy profile of the energy reflected from the specimen 114.

In addition to generation of a time-energy profile, other analyses can also be performed on the signals returned from the piezoelectric force sensor 160a. For example, the amount of work associated with the impact can be evaluated by integrating the force applied to the tapping rod 120 with respect to the displacement of the specimen. The force applied to the tapping rod 120 during its impact with the object 112 can be measured using the piezoelectric force sensor 160a. After the impact, the amount of work depends partially on the quantity of defects present in the object 112. In particular, defects in the object 112 dissipate the kinetic energy of the rod 120 as it impacts the object 112, thereby reducing the amount of elastic energy available to be returned to the tapping rod 120.

In one embodiment, a comparison of the amount of elastic energy returned to the tapping rod 120 and the total work associated with the impact can be used to determine the quantity and nature of structural defects present in the object 112. In another embodiment, a Gaussian distribution peak or other mathematically derived peak, may be fitted to the measured percussion response such as energy, stress or force data. The residue or mean error may be used to determine how closely the measured data are representative of a defect-free object 112.

Figure 16B:
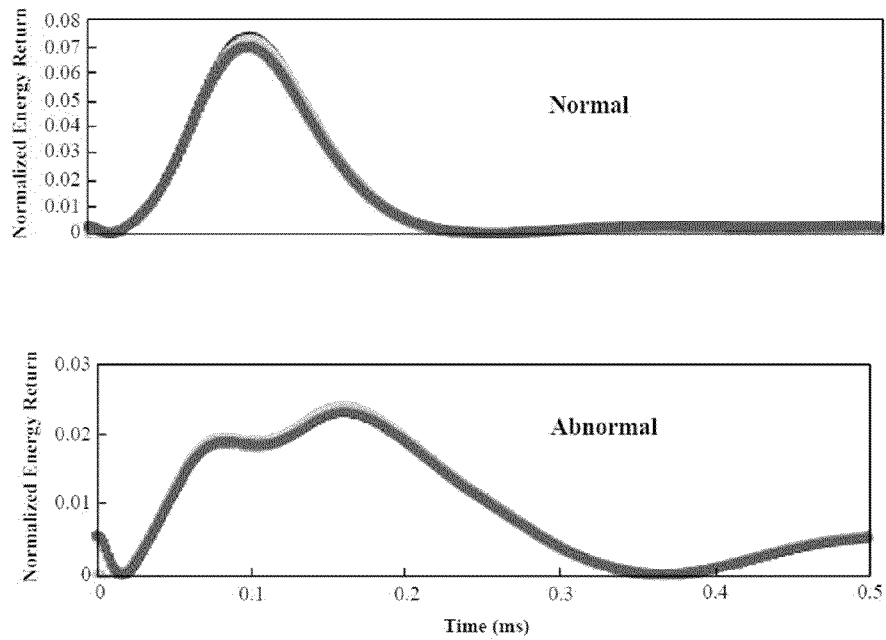
FIG. 16b shows the graphs of a normal and abnormal structure after numerous measurement and how it compares with the ideal fit.

FIG. 16b shows examples of the shape of time versus percussion response, for example, time-energy profiles generated on tooth. For a normal tooth, a smooth, bell-shaped curve is generated, as shown. For an abnormal tooth, a curve having various shapes, for example, asymmetric profile or multiple peak profile is generated, as shown. Even though the profiles shown are in reference to tooth, the profiles may be generalized to any other objects mentioned above, whether anatomical or industrial or physical.

The device and system of the present invention may also be used in other damping factor measurements, such as those disclosed in U.S. Pat. Nos. 5,476,009 and 5,614,674; non-invasively determining the loss in density of a discrete piece of biological tissue, such as that disclosed in U.S. Pat. Nos. 5,836,891, and 5,402,781; a modal damping factor of a structure, such as that disclosed in U.S. Pat. No. 5,652,386; for detecting an incipient flaw in an object by measurement of the specific damping capacity of the object, such as disclosed in U.S. Pat. No. 4,231,259; non-destructive testing, such as disclosed in U.S. Pat. No. 4,519,245; instruments used for causing vibration and analyzed by Fourier Transform, as disclosed in U.S. Pat. No. 5,951,292; for detecting the stability of a tooth in the gum or an implant in the body, as disclosed in U.S. Pat. No. 6,918,763; for determining the mobility of a tooth or dental implant, such as disclosed in U.S. Pat. No. 5,518,008; or any other measurements using a percussion instrument for generating vibration in an object; the contents of which are hereby incorporated by reference in their entirety.

Healthy teeth and well-integrated implants exhibit a low level of energy dissipation with a smooth, symmetric, bell-shaped time-elastic energy profile, as shown in the upper curve of FIG. 16b. As used in this context, the term "elastic energy" refers to the elastic energy imparted to the rod 120 of the percussion instrument 100. The elastic energy $E_e$ is given by $E_e = kF^2$, where the constant k varies inversely with the effective elastic modulus of the tapping rod 120 and where the force F is proportional to both the mass of the tapping rod 120 and the maximum deceleration of the tapping rod 120 as a result of the stress wave created from the impact.

Figure 27:
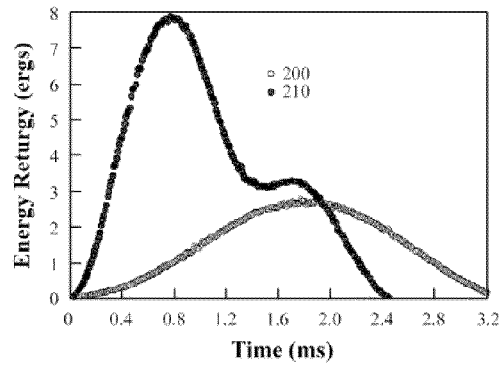
FIGS. 27 and 28 show time percussion response profiles generated by the system and method of the present invention.

In contrast to well-integrated implants, implants suffering from poor osseointegration, bone loss, internal defects, or a damaged structure typically may exhibit a nonuniform time versus percussion response profile. For example, FIG. 27 illustrates a "normal" time versus percussion response profile 200 for a healthy implant, as well as an "abnormal" time versus percussion response profile 210 for an implant structure that is not well-integrated, as is also shown in FIG. 16b for normal and abnormal implant. As illustrated, the time versus percussion response profile 200 for the healthy tooth has a smooth, symmetric, bell shape, whereas the time versus percussion response profile 210 for the abnormal implant structure is not smooth and symmetric, or may have a secondary maxima 212. The shape of the time versus percussion response profile for the abnormal implant structure indicates that defects, such as loose screws, a damaged internal structure, bone loss at the bone/implant interface, or poor osseointegration, are present. In addition to secondary maxima, other abnormalities in the shape of the time versus percussion response profile that are indicative of structural defects include scattered data, asymmetries and irregular shapes.

Figure 28:
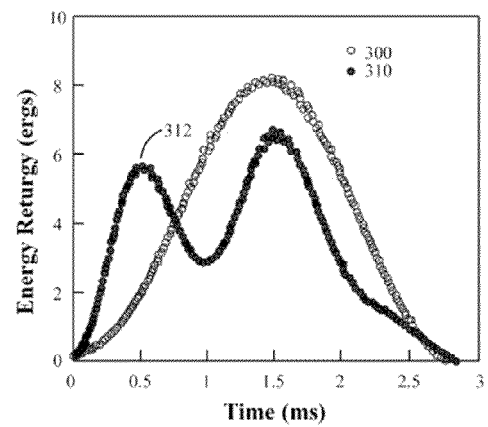

An additional example of this principle is provided in FIG. 28, which illustrates a "normal" time versus percussion response profile 300 of a well-integrated implant, as well as an "abnormal" time versus percussion response profile 310 for an implant structure that is not well-integrated. Both of these implant structures are located, for example, in the mouth of a heavily parafunctional elderly patient. As explained previously, the presence of the secondary maxima 312 indicates that defects, such as loose screws, a damaged internal structure, bone loss at the bone/implant interface, or poor osseointegration, are present at the implant site.

The foregoing examples illustrate that analysis of the time versus percussion response profile of a dental structure can provide information about the integrity and stability of that structure. These analysis techniques provide clinicians with an accurate, fast and simple tool that provides information on the stability of natural and prosthetic dental structures without requiring an invasive procedure. The tab and/or feature add to the repeatability of these measurements and thus produce smaller standard deviations.

For composite structures, the instrument of the present invention described above may also be used in fields other than dentistry. For example, such instrumentation may be used in assessing the local damping capacity of composite structures, such as layered honeycomb composites or any other structures. In particular, use of such instrumentation in the testing of composite structures advantageously allows the damping capacity of these structures to be evaluated without damaging the structures. The instrumentation disclosed herein is also light, portable, easy to use, quick and inexpensive as compared to conventional apparatuses for evaluating damping capacity.

Because damping capacity measures the ability of a material to absorb and isolate vibration, damping capacity is of particular interest with respect to materials used for acoustic insulation, such as in the aerospace, boating, bridges, arch structures, civil engineering and automotive engineering fields. Thus it is often sought to test the damping capacity of new materials under development, as well as conventional materials after sustained use.

As an example, layered honeycomb structures generally have a relatively high damping capacity, and thus are often used as acoustic insulators in these fields. Typical layered honeycomb structures have two relatively thin facings that have high strength and stiffness. The facings enclose a honeycomb core structure that is relatively thick, but lightweight and with high strength in the direction perpendicular to the facings. For example, the honeycomb core structure may include a Nomex® honeycomb core, available from E.l. du Pont de Nemours and Company (Wilmington, Del.). The facings and the core are generally bonded together, either mechanically or with adhesives (such as, for example, with a phenolic resin or other structural or reactive adhesive), thus giving the structure composite properties. In the composite structure, the facings may carry bending stresses, while the core carries shear stresses. When exposed to acoustic vibrations for a prolonged period, degradation in the bonds between the layers, as well as in the honeycomb core itself, may cause a layered honeycomb core structure to have diminished acoustic insulation capacity.

Figure 29:
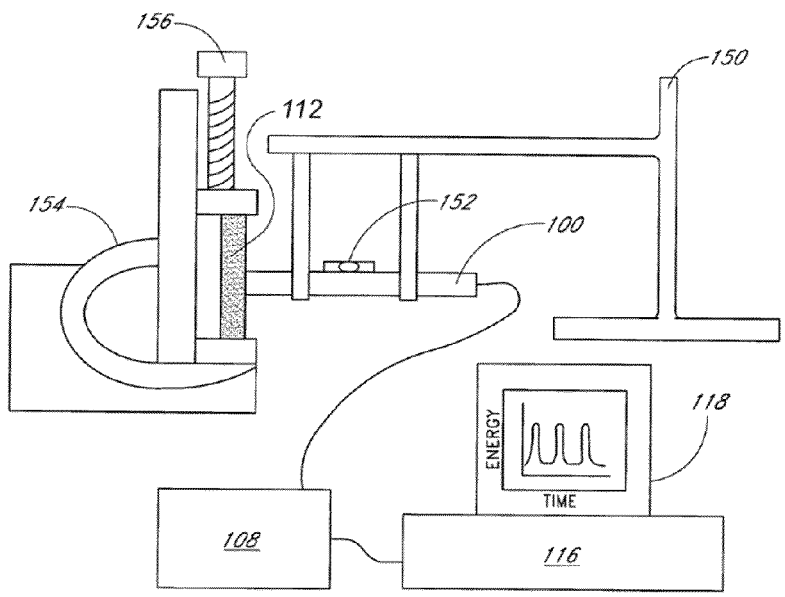
FIG. 29 shows a schematic of an embodiment of the system and instrument of the present invention.

Referring now to FIG. 29, an exemplary embodiment of an apparatus configured for evaluating the damping capacity of composite structures is illustrated. The apparatus includes an embodiment of the system 100 of the present invention mounted within a secured bracket 150 configured to stabilize the percussion instrument 100. The system 100 may optionally be outfitted with a level 152 to assist in aligning the instrument 100 substantially perpendicular to an object or specimen 112 that is to be tested. In an exemplary embodiment, the specimen 112 is mounted in an angle vise 154 having a hand-adjustable vise drive 156, thereby allowing the specimen 112 to be held in compression during testing. In a modified embodiment, the angle vise 154 may be outfitted with rubber grips to reduce external sources of vibrational noise that could be detected by the system 100.

Still referring to FIG. 29, the system 100 is electronically connected to a computer 164 via an instrumentation interface 168. In such embodiments, the computer 164 may include a display 180 capable of graphically presenting data generated by the system 100, such as a time versus percussion response profile.

The testing apparatus illustrated in FIG. 29 may be used to evaluate the damping capacity of a wide variety of materials. For example, in one application, this apparatus can be used to evaluate the damping capacity of layered honeycomb composite specimens. In such an application, the specimen 112 to be tested is mounted in the angle vise 154, which is tightened using the vise drive 156 to a torque of approximately 2765 gcm, although in other embodiments, the specimen 112 may be loaded to a different torque.

In an exemplary embodiment, the instrument of the present invention can detect damping difference between different restorative materials to help choose the most biomemetic material to protect the mouth from damaging impact, such as normal parafunctional activities, repetitive loading activity and not limited to just extraordinary events. In addition, it can also be employed to evaluate which type of implant-supported restoration (for example, CAD/CAM composite resin and zirconia abutments combined with CAD/CAM composite resin and ceramic onlays and crowns) would respond more biomimetically to physiologically relevant dynamic loading, loss coefficient measurements may be employed. After implant/abutment/restoration assembly may be made with a chosen material, the instrument of the present invention may be positioned perpendicularly to the coronal third of the buccal surface of each restoration. The tooth may be held at an angle to keep the probe horizontal, as shown in FIG. 26b. The measurements for a chosen object or specimen 112 may be used to predict the most suitable material to be employed for the implant, restoration, etc. For example, composite resin onlays bonded to zirconia implant abutments may present the most biomimetic dynamic response to load when compared to teeth in a simulated bone support structure.

Figures 19, 19A:
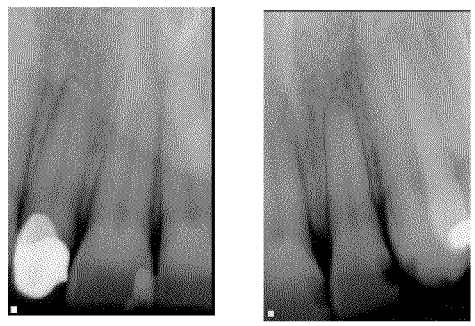
FIGS. 19, 19a-g depicts 3 teeth tested with the system and method of the present invention and other existing methods.
Figure 19B:
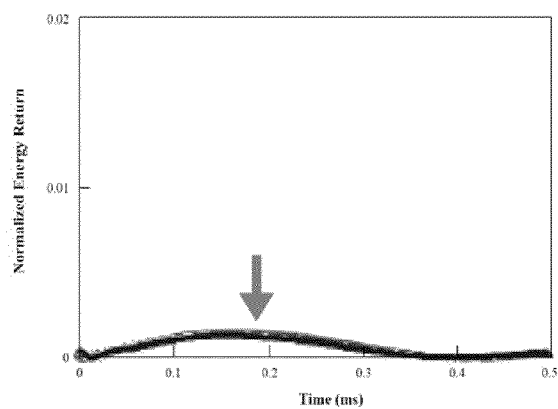
Figure 19C:
Figure 19D:
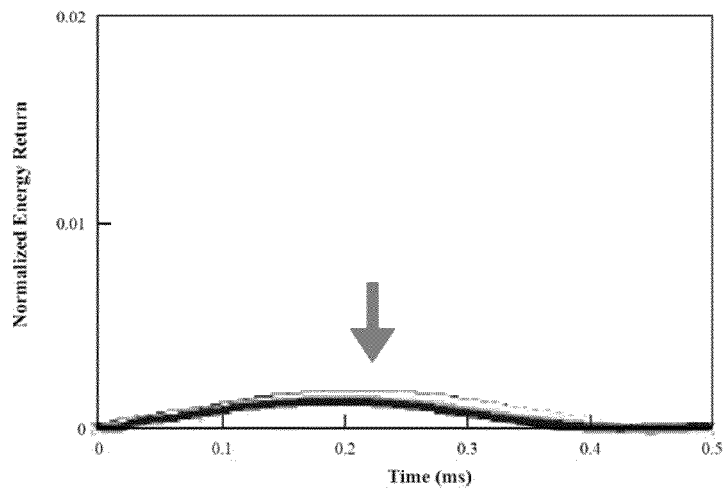
Figure 19E:
Figure 19F:
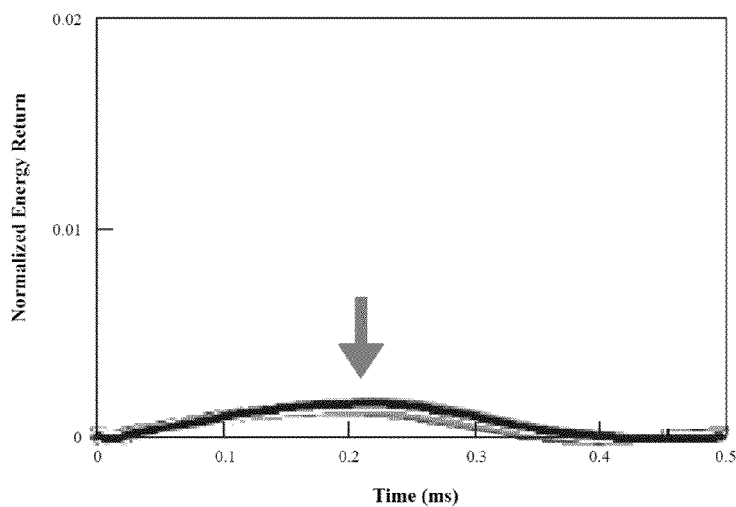

In other exemplary embodiments, the instrument of the present invention may also be employed to test the looseness of a tooth structure right after dental work or dental implanting. When a tooth structure is just loose, without defects or cracks as noted above, it may have a relatively flat time versus percussion response profile, as shown in FIGS. 19b, d and f, or FIGS. 20, 20a-b when they are just loose prior to dental work and following orthodontic movement of the teeth. After allowing time for the dental work to settle and the bone to heal around the new structure and orthodontic positioning of the teeth, a normal bell-shaped profile is shown in FIGS. 20c-e. With another exemplary embodiment, the present invention may be used by orthodontists to measure the stability of teeth after orthodontic movement.

Figure 21:
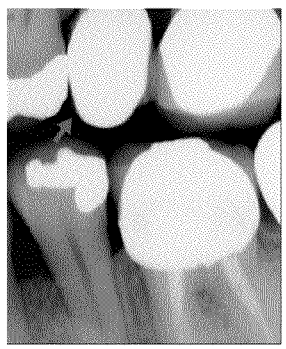
FIGS. 21 and 21a-b show X-rays and time percussion response profiles using the system of the present invention of the same tooth.
Figure 21A:
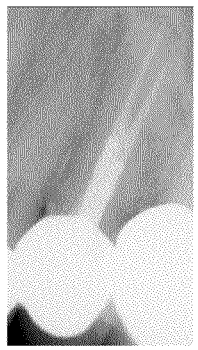
Figure 21B:
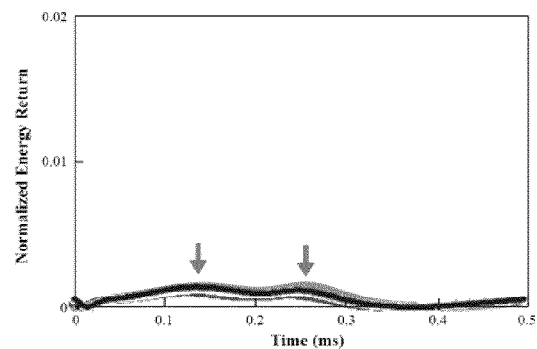
Figure 22:
FIGS. 22 and 22a show the visual and time percussion response profile using the system of the present invention of the same tooth.
Figure 22A:
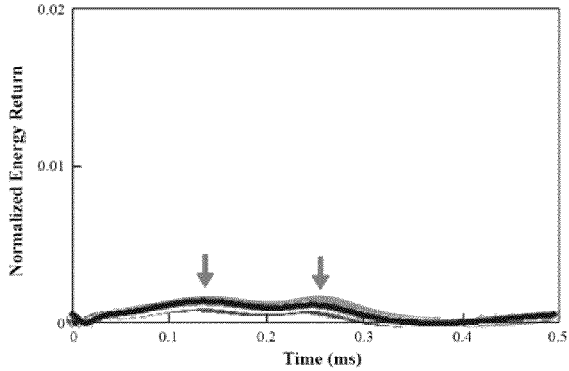

In addition, low or flat profiles with abnormal or multiple peaks, as shown in FIGS. 21b and 22a, may correspond to extreme mobility and structural breakdown failure, indicating that the tooth may be not restorable.

In any of the above mentioned measurements, the sleeve 108 of the present invention may be fitted to other commercially available handpieces that are not adapted for contact with an object under measurement, so that the advantages of the present invention may also be realized. Any suitable manner of attachment of the sleeve 108 to the available handpieces may be used to modify the handpieces.

As noted, in some embodiments, the sleeve 108 and/or portions of the housing 132 may include coatings capable of eliminating, preventing, retarding or minimizing the growth of microbes, thus minimizing the use of high temperature autoclaving process or harsh chemicals and may increase the kind and number of materials useful as substrates for making such tools or instruments.

The coatings may include chemical anti-microbial materials or compounds that are capable of being substantially permanently bonded, at least for a period such as the useful life sleeve 108, or maintain their anti-microbial effects when coated with the aid of coating agents, onto the exposed surfaces of the sleeve 08. In one example, the chemicals may be deposited on the surface of the sleeve 108 by covalent linkage or linkages.

In other embodiments, the coatings may include chemical antimicrobial materials or compounds that may be deposited in a non-permanent manner such that they may dissolve, leach or otherwise deliver antimicrobial substances to a useful field, such as the mouth, during use.

In still other embodiments, the coatings may include sources of anti-microbial agents that may leach and/or release agents in a moist environment or upon contact with moisture. These sources may be incorporated into the substrate materials used for manufacturing the sleeve, or included in the coatings coated on the exposed surfaces of the sleeve 108. Incorporation of the sources is especially suited to polymeric substrates.

Chemical antimicrobial materials or compounds may include a variety of substances including, but not limited to antibiotics, antimycotics, general antimicrobial agents, metal ion generating materials, or any other materials capable of generating an antimicrobial effect. Chemical antimicrobial materials or compounds may also be selected to, for example, minimize any adverse effects or discomfort to the patient.

The anti-microbial compound may include, but are not limited to, antibiotics, quaternary ammonium cations, a source of metal ions, triclosan, chlorhexidine, and/or any other appropriate compound or mixtures thereof.

In yet further embodiments, antimicrobial activity may be achieved by utilizing the antimicrobial properties of various metals, especially transition metals which have little to no effect on humans. Examples may include sources of free silver ions, which are noted for their antimicrobial effects and few biological effects on humans. Metal ion antimicrobial activity may be created by a variety of methods that may include, for example, mixing a source of a metal ion with the material of a dental instrument during manufacture, coating the surface by methods such as plasma deposition, loosely complexing the metal ion source by disrupting the surface of the dental instrument to form affinity or binding sites by methods such as etching or coronal discharge, and depositing a metal onto the surface by means such as electroplating, photoreduction and precipitation. The sleeve 108 surface may then slowly release free metal ions during use that may produce an antimicrobial effect.

In some embodiments, the source of metal ions may be an ion exchange resin. Ion exchange resins are substances that carry ions in binding sites on the surfaces of the material. Ion exchange resins may be impregnated with particular ion species for which it has a given affinity. The ion exchange resin may be placed in an environment containing different ion species for which it has a generally higher affinity, causing the impregnated ions to leach into the environment, being replaced by the ion species originally present in the environment.

In one embodiment, a sleeve may include an ion exchange resin containing a metal ion source, such as, for example, silver. Ion exchange resins containing metal ion sources may include, for example, Alphasan® (Milliken Chemical), which is a zirconium phosphate-based ceramic ion exchange resin containing silver. An ion exchange resin may be coated onto the sleeve 108 or it may be incorporated into the material of the sleeve 108.

In yet another embodiment, the sleeve 108 may be made from natural plant materials, natural material coating or blends thereof, having inherent antimicrobial effects. Such materials include materials like bamboo, believes to possess antimicrobial activity due to some novel chitin-binding peptides.

EXAMPLES

Example 1

In Vitro Studies of Bone Density

Implants used for this study were four threaded titanium implant geometries from:

1 and 2. Nobel Biocare (TiO2 coated, 13 mm long): Branemark Mark IV (max. diameter 4 mm); Replace selected tapered (max. diameter 4.3 mm);

3 and 4. Dentsply (13 mm long, 5.5 mm max. diameter); Frialit-2 (stepped design; XIVE (designed for immediate loading).

Procedures:

2.5×2.5×4 cm foam blocks were fabricated. The implants were "surgically" placed by the manufacturers. Holes were manually drilled in the simulated bone block, then the implants were placed with a torque wrench. Testing abutments were attached to the implants and the blocks placed in a vise with consistent mounting displacement. Three measurements (30 percussions) were performed for each specimen.

Results of the testing are shown in FIGS. 10 and 10a for 1 and 2; and 11 and 11a for 3 and 4. These samples would have produced similar graphs, adjusting for slight differences in the materials themselves. However, the graphs showed differences, even though the objects were identically prepared, but with different operators or same operator using slight variation in technique, for example, different sized-holes might have been drilled for mounting the object. These differences were picked up by the instrument, showing in the difference in graphs, showing that differences in the surrounding environment were revealed by the instrument of the present invention.

Example 2

Evaluation of the Importance of Buccal Percussion Loading

Buccal percussion loading, as mentioned above, is typically the more dangerous form of loading. In general, occlusal loading induces relatively low stresses. The working and/or nonworking motion produces side loading and induces much higher stresses that may generate a high stress concentration at external and internal surfaces and below margin. Thus, an embodiment of the present invention was used to perform the test below.

Procedure:

Using the system of the present invention, with loadings such as that shown in FIG. 12, measurements were made. The instrument loading of a maximum force of 1-15 Newtons were used in general, with maximum loadings chosen depending on the object or specimen. The tapping rod was free-floating. The kinetic energy was controlled. The impact velocity was 60 mm per second.

The instrument of the present invention was placed upon the object, as depicted in FIG. 26b. Using the calculations depicted in the FIG. 13, the tapping rod had a mass of 8 grams. The input energy, U was 0.5 mv2, i.e., the kinetic energy of the tapping rod. The maximum force (F) was used to determine the energy dissipated (D). Deceleration, a, was measured and the return energy, ER=U-D was calculated. The dynamic response measured after impact of the object with the instrument of the present invention was made and depicted in FIG. 16. Loss coefficients and energy return versus percussion response graphs were produced using the equations depicted in FIGS. 14 and 15. The resultant graphs, as shown in FIG. 16b, depicted what is normal and abnormal. For normal structure, a smooth, almost bell-shaped graph was obtained. For an abnormal structure, which could have any of the defects or cracks, as noted previously, an irregular graph was generated.

Example 3

Finite Element Analysis

This analysis method involved the use of numerical models to simulate actual testing using the system and method of the present invention.

Figure 24:
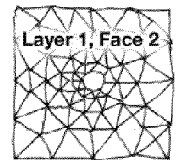
FIGS. 24 and 24b show a defect free composite laminated plate and a composite laminated sample with a defect placed in the center of the sample between layers, respectively.
Figure 24A:
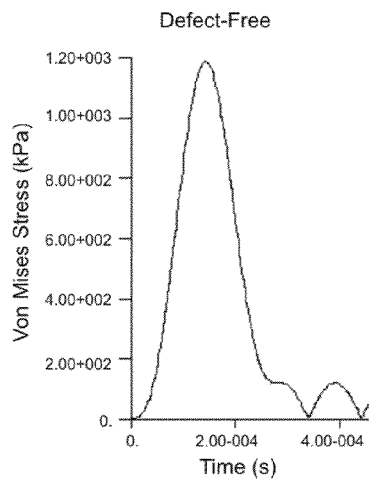
FIGS. 24a and c show percussion response graphs for the composites of 24 and 24b, respectively, using Finite Element Analysis.
Figure 24B:
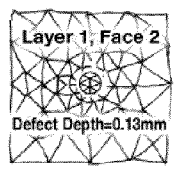

Layered structures were used in the present experiment, one structure with no defect in the laminated composite layer (FIG. 24) and one with a defect in the center of the composite laminated layer (FIG. 24b)

Figure 23:
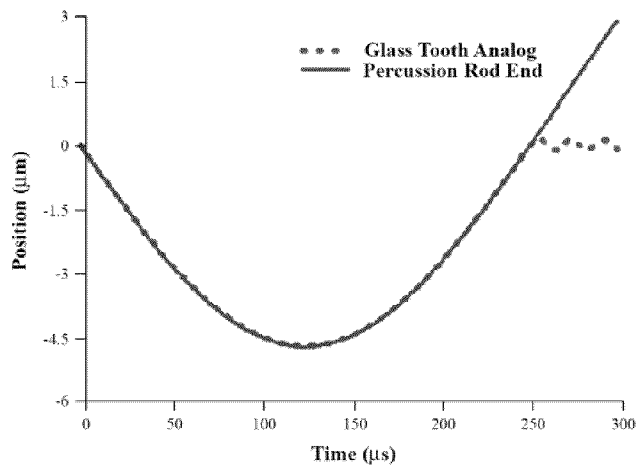
FIG. 23 shows data from finite element analysis, using a glass rod to simulate a tooth and a curve created by impact in a finite element model.

FIG. 23 measured the residence time of the tapping rod against an object. A glass rod or cylinder was used to simulate a tooth structure for the measurement shown in FIG. 23. The graph in FIG. 23 showed the relative positions of the tapping rod and glass rod with time. When tapping rod tapped the surface of the glass rod, their respective positions coincided at the start. As time progressed, the tapping rod gradually moved away from the surface of the glass rod and at 250 μsec., they separated, indicating the residence time of the tapping rod on the surface to be 250 μsec.

Figure 24C:
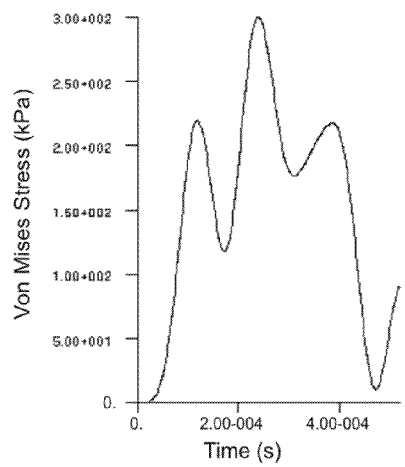
Figure 25:
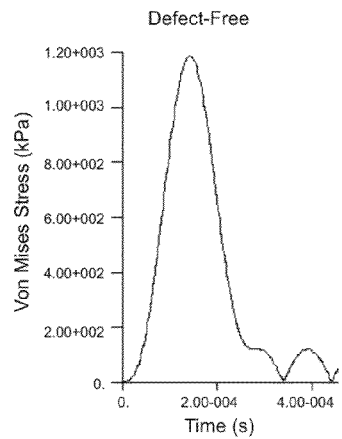
FIGS. 25 and 25a show a repeat measurement of composites of FIGS. 24 and 24b.
Figure 25A:
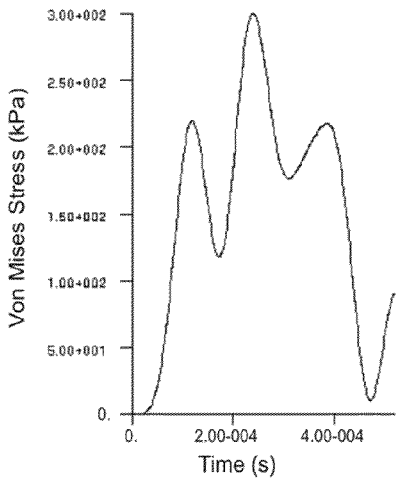

Using this residence time, analysis on the composite plates of FIGS. 24 and 24b were made. Results are shown in FIGS. 24a and 24c, respectively. The graph in FIG. 24c confirmed the defect in the composite layers, a delamination of the layers in the composite structure. A repeat measurement was made and the results are shown in FIGS. 25 and 25a. Thus, the analysis may be used to simulate the system and method of the present invention.

Example 4

To Evaluate Loss Coefficient for Determining the More Biomemetically Compatible Material to Use in Implants, Restorations, Etc.

To evaluate the LC of extracted human teeth and assess which type of implant-supported restoration (CAD/CAM composite resin and zirconia abutments combined with CAD/CAM composite resin and ceramic onlays and crowns) would respond more biomimetically to physiologically relevant dynamic loading, the instrument of the present invention, as shown in FIG. 27b was used to measure the loss coefficient (LC) of some materials. More suitable materials generated bell-shaped graphs similar to the upper graph of FIG. 16b, while less suitable materials generated irregular graphs similar to that of the lower graph of FIG. 16b or demonstrated a LC value that was much lower than that found in a natural tooth, thus facilitating the choice of materials prior to restoration without having to rely on trial and error, which can be time consuming and expensive if re-treatment is indicated, while exposing patients to discomfort and potential danger of receiving more damage.

Example 5

Sensitivity and Accuracy of the Instrument of the Present Invention to Measure Cracks, Defects, Etc.

Figure 17:
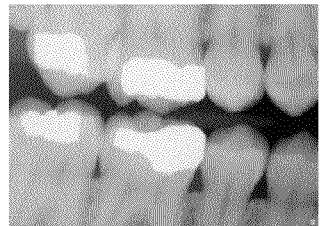
FIGS. 17 and 17a-h depict a tooth tested with the system and method of the present invention and other exiting methods.
Figure 17A:
Figure 17B:
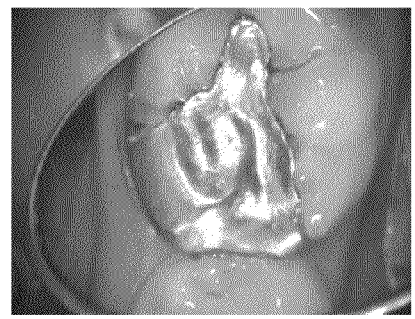

Actual human teeth inside the mouth of a patient were used in this study. The information of FIGS. 17 and 17a-h were generated on the same tooth. FIGS. 17 and 17a showed radiographs of a patient's tooth showing no pathology. FIG. 17b shows an image of an older alloy restoration also showing no pathology. Thus the radiographs and visual inspection both showed that the tooth was normal, i.e., no defects or cracks. Based on these usual testing methods, a symmetrical or bell-shape time versus percussion response profile or graph would be expected (or one similar to the light shade curve in FIG. 17c, calculated based on the formulae in FIGS. 13, 14 and 15).

Figure 17C:
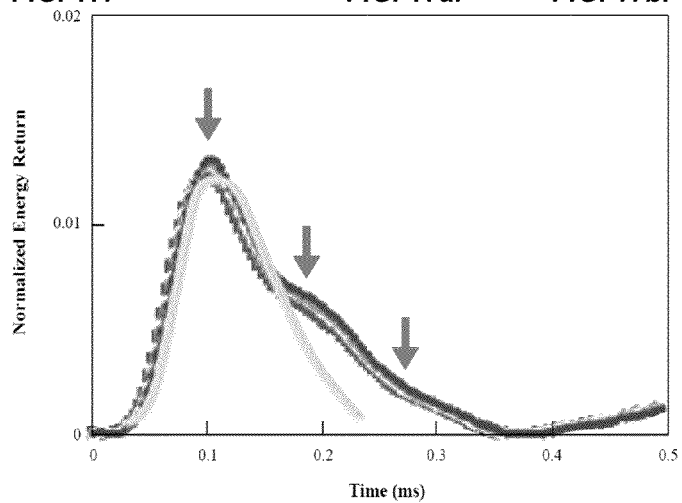

However, on the same day, a time versus percussion response graph was made using the instrument of the present invention as shown in FIGS. 1 and 16, using the sleeve with a tab, as shown in FIG. 27d. FIG. 17c showed the same tooth as in FIGS. 17 and 17a, showing an abnormal time versus energy return percussion response graph indicating some abnormality. The abnormal graph indicated that the tooth had cracks at different places within the structure of the old filling, as indicated by the arrows in FIG. 17c, with an asymmetrical or non-bell-shaped curve. Numerous measurements were performed and these all showed the same irregular shape, as well as reproducibility of the measurements. Thus, the instrument of the present invention was capable of detecting any abnormality. The abnormal secondary peaks were indicated by arrows in the FIG. 17f also, showing cracks.

Figure 17D:
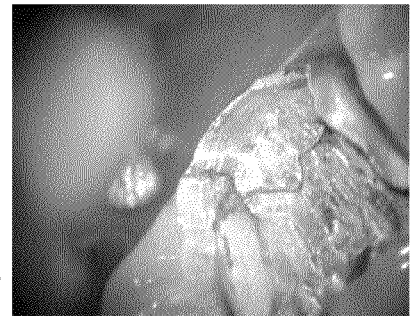

FIG. 17d showed an image of the same tooth as FIG. 17 during removal of the older alloy filling, showing a significant crack in the alloy filling which had developed microleakage and gross decay underneath the filling. The fractured alloy filling was leaking and allowing decay to develop under the old filling. This confirmed the abnormality detected by the instrument of the present invention.

Figure 17E:
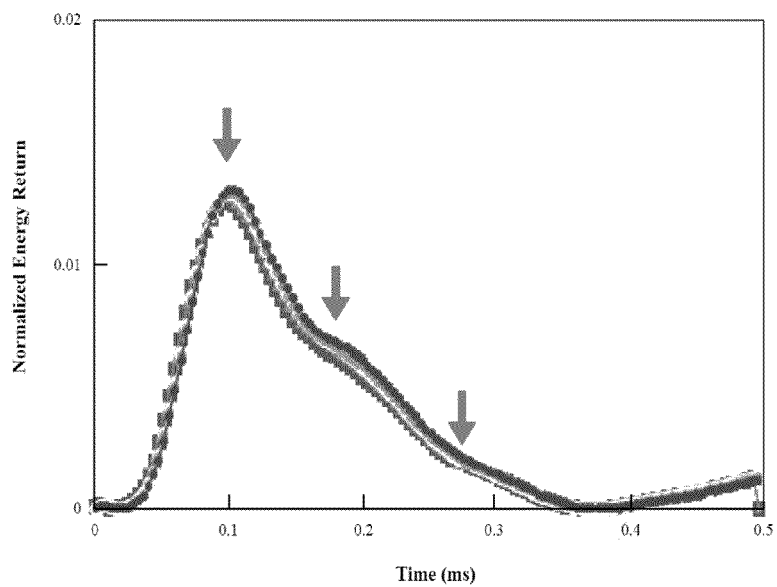
Figure 17F:
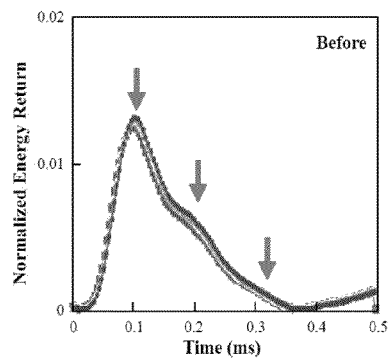

FIGS. 17e and 17f showed the same pre-treatment time versus percussion response graph prior to the alloy removal. Rechecked showed that the crack measurements were reproducible, as shown in FIGS. 17e-f.

Figure 17G:
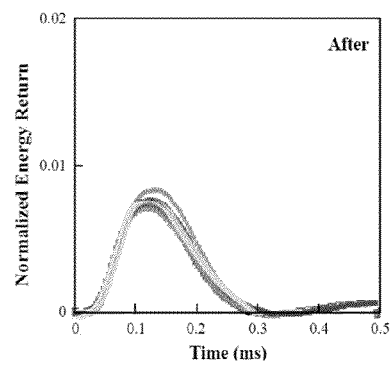

FIG. 17g showed the time versus percussion response graph taken the same day as FIG. 17e after the old alloy and decay were removed and a new well sealed composite restoration was placed. The time versus percussion response graph of the tooth was normal again.

Figure 17H:
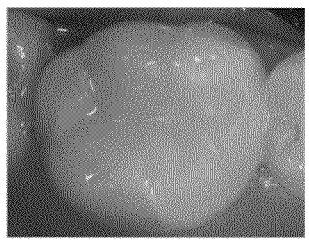

FIG. 17h shows the new composite restoration that tested normal in FIG. 17g after the older alloy restoration was replaced earlier in the day. FIGs. The drama of this example was that the energy return profile of 17f and 17g were for the same tooth on the same day, the difference being that the old filling and decay was removed and a fresh bonded composite restoration was placed, which was the photo 17h.

Figure 18:
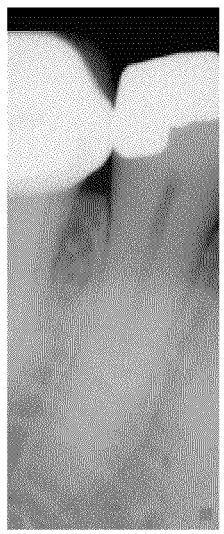
FIGS. 18 and 18a-f show a repeat procedure on a different tooth to that of FIGS. 17, 17a-h.
Figure 18A:
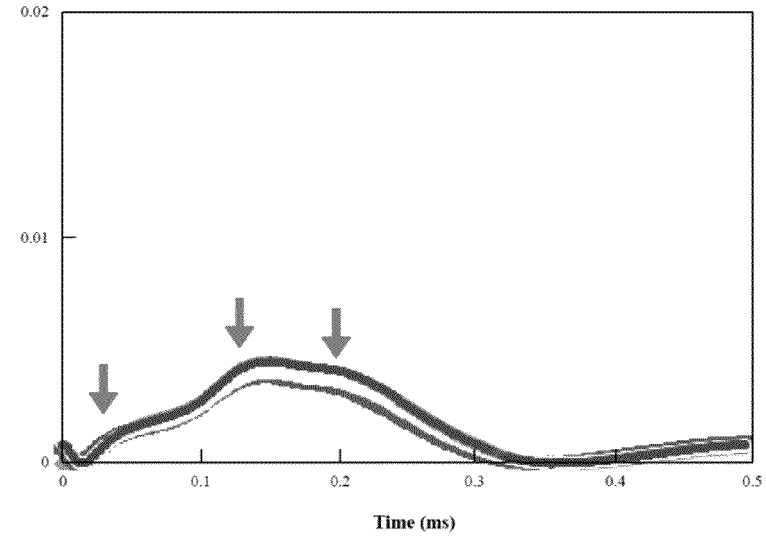
Figure 18B:
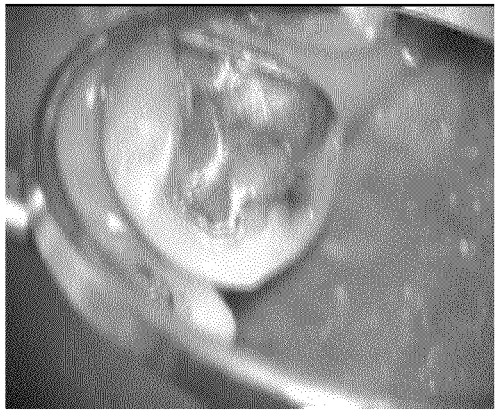
Figure 18C:
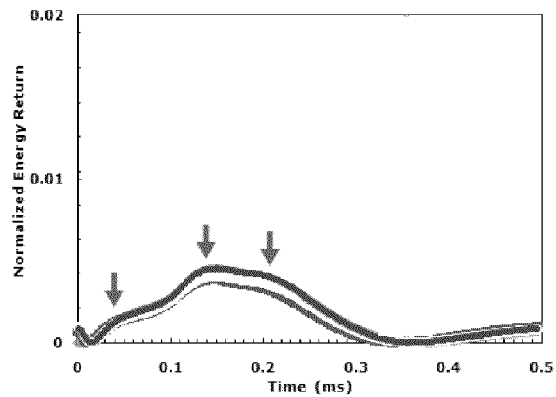
Figure 18D:
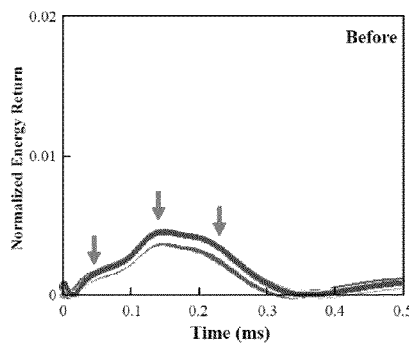
Figure 18E:
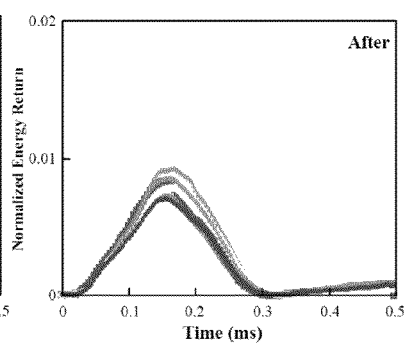
Figure 18F:
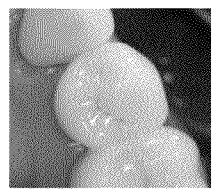

This experiment was repeated with another tooth. The results are shown in FIGS. 18, 18a-f. FIG. 18 showed a tooth with no pathology shown on a radiograph. FIG. 18a showed an abnormal time versus percussion response graph for the tooth shown in FIG. 18 radiograph. FIG. 18b is a photograph of the tooth evaluated in FIGS. 18 and 18a showing no significant pathology upon visual inspection. However, upon removal of the filling, deep decay was present and microleakage under the old filling. FIGS. 18c and 18d and the same graph repeated showing the defect prior to removal of the old alloy. FIG. 18e shows a normal ERG for the same tooth after the final restoration was completed. FIG. 18f showed the same tooth shown in 18b with the new restoration that was testing normally. This again indicated the accuracy of the instrument of the present invention.

Figure 19G:

In addition, as mentioned above, the system of the present invention may also be used to detect looseness of a tooth structure right after dental work. FIGS. 19-19g show pre-treatment radiographs and time versus percussion response graphs for three different upper anterior teeth.

FIGS. 19, 19a, c, e and g showed new dental work with new fillings, i.e., the white spots represented fillings and a gold crown. The graphs produced with an embodiment of the instrument of the present invention was normal, i.e. Symmetrical, but low, as shown in FIGS. 19b, d and f, and FIG. 20. The tooth was loose and not stable due to the patient recently completing orthodontic movement of his teeth, though structurally sound.

Figure 20:
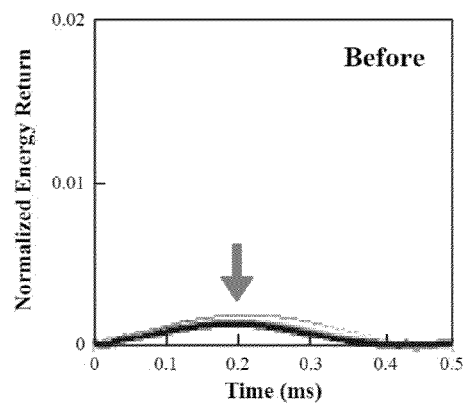
FIGS. 20, 20a-f shows a tooth and its time percussion response profile before and after dental work, using the system of the present invention.
Figure 20A:
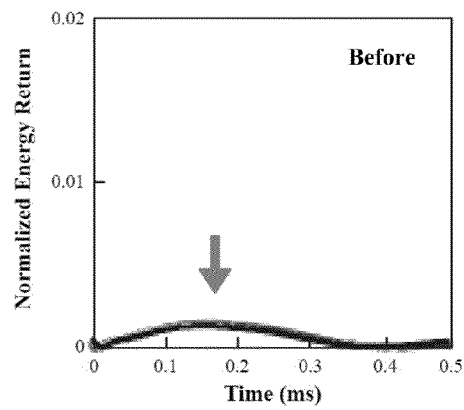
Figure 20B:
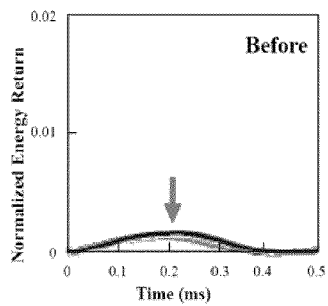
Figure 20C:
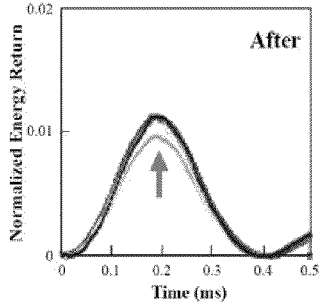
Figure 20D:
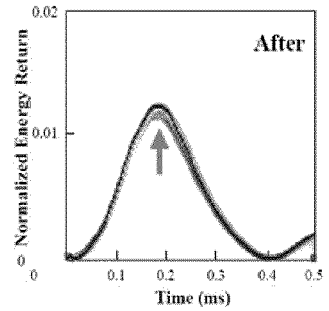
Figure 20E:
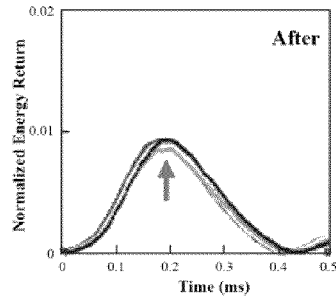
Figure 20F:
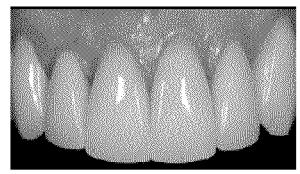

FIGS. 20, 20a and 20b also showed the time verus energy return percussion response curves of teeth that were loose prior to treatment. FIGS. 20c, 20d, 20e were the post restoration time versus percussion response graphs for the same teeth. FIG. 20f showed the final photo of the restored and structurally normal teeth. The graphs were higher here because the teeth were more stable in the bone after treatment. The bone had been able to remodel post orthodontic treatment. Thus, after allowing time for the dental work to settle and the tooth structure more firmly attached, a normal bell-shaped profile resulted with higher profiles.

On the other hand, when low or flat profiles with abnormal or multiple peaks, as shown in FIGS. 21b and 22a, were produced, extreme mobility and structural breakdown failure were indicative of the fact that the tooth was not restorable. FIGS. 21 and 21a were x-rays of the tooth used in FIG. 21b, showing multiple fillings and FIG. 22 showed the deep gross decay under this old crown, deep into the root structure that this tooth needed an extraction due to extensive terminal decay. FIG. 22a showed the time energy profile made using the system of the present invention of the same tooth, showing an extreme abnormality in shape and height.

Having described the invention by the description and illustrations above, it should be understood that these are exemplary of the invention and are not to be considered as limiting. Accordingly, the invention is not to be considered as limited by the foregoing description, but includes any equivalents.

The invention claimed is:

1. A device for determining structural characteristics of an object, in a non-destructive manner, comprising:
    a housing with an open end and a longitudinal axis;
    an energy application tool mounted inside the housing for axial movement along the longitudinal axis of the housing, said energy application tool having a retracted form and an extended form;
    a sleeve protruding from the open end of the housing for a distance, said sleeve having an object contact surface on at least a portion of its open end;
    a tab extending from a portion of the sleeve substantially parallel to the longitudinal axis of the housing and having an object contact surface substantially perpendicular to said object contact surface of the sleeve; and
    a drive mechanism supported inside the housing, said drive mechanism adapted for moving the energy application tool between the retracted and extended form;
    wherein the contact of said object contact surface of said tab with said object stabilizes the placement of said energy application tool in relation to said object by decreasing movement of said device in a direction other than along said longitudinal axis during measurement.

2. The device of claim 1 wherein said tab is adapted for minimizing the motion of the object after application of energy in any direction other than a direction of energy application.

3. The device of claim 1 wherein said object comprises an anatomical object, an industrial or physical object, or combinations thereof.

4. The device of claim 1 wherein said tab comprises a contact surface substantially mirroring the contour of a surface of the object to which it comes into contact during use for aiding in reproducibly positioning of the device on the object.

5. The device of claim 1 wherein said sleeve comprises a vibration damping material, an acoustic damping material, a material having a vibrating attenuating coating, or combinations thereof.

6. The device of claim 1 wherein said sleeve and tab comprises same material or different materials having similar thermal expansion properties.

7. The device of claim 1 wherein said drive mechanism comprises a measuring and/or sensing device positioned within said handpiece adapted for measuring and/or sensing the displacement of the energy application tool or response of the object after energy application.

8. The device of claim 7 wherein said measuring and/or sensing device comprises a piezoelectric force sensor or a linear variable differential transformer.

9. A system for determining structural characteristics of an object, in a non-destructive manner, comprising:
a handpiece comprising:
a housing with an open end and a longitudinal axis;
an energy application tool mounted inside the housing for axial movement along the longitudinal axis of the housing;
a sleeve protruding from the open end of the housing, said sleeve having a tab extending from a portion thereof for aiding in reproducibly positioning of the handpiece directly on said object, by contacting a first surface of said object with at least a portion of its open end, said tab being substantially parallel to the longitudinal axis of the housing and contacting said object at a second surface substantially perpendicular to said first surface; and
a drive mechanism supported inside the housing, said drive mechanism adapted for moving the energy application tool between a retracted and an extended form; and
a computer coupled to said handpiece adapted for determining structural characteristics of the object;
wherein said contacting of said tab with said object stabilizes said handpiece to minimize the movement of the tool in directions other than along said longitudinal axis during measurement.

10. The system of claim 9 wherein said determining structural characteristics of an object comprises the generation of time versus percussion response graphs or loss coefficients of the object after application of energy by the energy application tool on the object.

11. The system of claim 10 wherein said time versus percussion response graph comprises a time-energy, time-stress, time-force, or acceleration profile.

12. The system of claim 10 wherein said tab is adapted for minimizing the motion of the object after application of energy in any direction other than a direction of energy application.

13. The system of claim 10 wherein said object comprises an anatomical object, an industrial or physical object, or combinations thereof.

14. The system of claim 9 wherein said structural characteristics of the object comprises densities; bone densities or a level of osseointegration; defects, inherent or otherwise; cracks, fractures, microfractures, microcracks; loss of cement seal; cement failure; bond failure; microleakage; lesion; decay; cement failure; bond failure; vibration damping; acoustic damping; delamination; or combinations thereof of said object or a foundation to which said object is attached.

15. The system of claim 9 wherein said structural characteristics comprises information as to the location of defects, inherent or otherwise, cracks, fractures, microfractures, microcracks, microleakages, lesion, decay, delamination; Information on the suitability of a material for use in dental work prior to the actual work; determination of whether a tooth structure is restorable prior to the actual work; information on whether a restorative procedure is successful; information on when the tooth structure that underwent any procedure has been remodeled; information on the looseness of tooth structure before and after dental work; or combinations thereof.

16. The system of claim 9 wherein said computer comprises a data analyzer configured to evaluate a shape of the time versus percussion response profile.

17. The system of claim 16 wherein the data analyzer is programmed to count the number of energy maxima reflected after the energy application tool impacts the object.

18. A portable device for determining structural characteristics of an object, in a non-destructive manner, comprising:
a handpiece housing for housing a movable energy application tool;
a sleeve located on said housing, said sleeve having a tab extending from a portion thereof, said sleeve having an object contacting surface on at least a portion of its open end with said tab being substantially parallel to a longitudinal axis of the handpiece housing and substantially perpendicular to the object contacting surface of the sleeve for aiding in stabilizing and reproducibly positioning of the device against said object during measurement; and
a drive mechanism supported inside the housing and adapted for moving the energy application tool between a retracted and extended form, said drive mechanism comprising a sensing mechanism configured to detect energy, force, stress or acceleration reflected from the object or the displacement of the energy application tool over a discrete time period after the energy application tool impacts the object.

19. The device of claim 18 wherein said tab comprises a feature substantially orthogonal to the tab adapted for further aiding in positioning of the device on the object.

20. The device of claim 18 wherein said determining structural characteristics of an object comprises the generation of time versus percussion response graphs or loss coefficients of the object after application of energy by the energy application tool on the object.

* * * * *